US009682910B2

(12) United States Patent
Nandy et al.

(10) Patent No.: US 9,682,910 B2
(45) Date of Patent: Jun. 20, 2017

(54) SERIES OF SKIN-WHITENING (LIGHTENING) COMPOUNDS

(71) Applicant: Unigen, Inc., Seattle, WA (US)

(72) Inventors: Sandip K. Nandy, Olympia, WA (US); Jiyun Liu, Bothell, WA (US); Alexandre Mikhailovitch Nesterov, Olympia, WA (US); Carmen Hertel, Tacoma, WA (US); Abeysinghe Arrachchigae Papmapiya, Olympia, WA (US)

(73) Assignee: Unigen, Inc., Seattle, WA (US)

( * ) Notice: Subject to any disclaimer, the term of this patent is extended or adjusted under 35 U.S.C. 154(b) by 0 days.

(21) Appl. No.: 14/750,873

(22) Filed: Jun. 25, 2015

(65) Prior Publication Data
US 2016/0083322 A1 Mar. 24, 2016

Related U.S. Application Data

(60) Continuation of application No. 14/154,013, filed on Jan. 13, 2014, now Pat. No. 9,096,507, which is a continuation of application No. 13/722,394, filed on Dec. 20, 2012, now Pat. No. 8,658,838, which is a division of application No. 12/506,497, filed on Jul. 21, 2009, now Pat. No. 8,362,305.

(60) Provisional application No. 61/082,422, filed on Jul. 21, 2008.

(51) Int. Cl.
| | |
|---|---|
| *C07C 43/23* | (2006.01) |
| *C07C 39/15* | (2006.01) |
| *A61K 31/085* | (2006.01) |
| *A61K 31/05* | (2006.01) |
| *C07C 43/295* | (2006.01) |
| *A61K 31/09* | (2006.01) |
| *C07D 213/64* | (2006.01) |
| *A61Q 19/08* | (2006.01) |
| *C07D 263/57* | (2006.01) |
| *A61K 8/34* | (2006.01) |
| *A61K 31/4406* | (2006.01) |
| *A61K 31/357* | (2006.01) |
| *A61K 31/341* | (2006.01) |
| *C07C 45/74* | (2006.01) |
| *C07D 317/54* | (2006.01) |
| *C07D 307/12* | (2006.01) |
| *A23B 7/154* | (2006.01) |
| *A61K 8/49* | (2006.01) |
| *C07D 213/30* | (2006.01) |
| *C07C 45/67* | (2006.01) |
| *A23L 3/3481* | (2006.01) |
| *C07C 49/83* | (2006.01) |
| *C07D 307/42* | (2006.01) |
| *A61Q 19/02* | (2006.01) |
| *C07C 39/11* | (2006.01) |
| *C07C 49/84* | (2006.01) |

(52) U.S. Cl.
CPC ............ *C07C 43/295* (2013.01); *A23B 7/154* (2013.01); *A23L 3/3481* (2013.01); *A61K 8/345* (2013.01); *A61K 8/347* (2013.01); *A61K 8/4926* (2013.01); *A61K 8/4973* (2013.01); *A61K 31/09* (2013.01); *A61K 31/341* (2013.01); *A61K 31/357* (2013.01); *A61K 31/4406* (2013.01); *A61Q 19/02* (2013.01); *A61Q 19/08* (2013.01); *C07C 39/11* (2013.01); *C07C 39/15* (2013.01); *C07C 43/23* (2013.01); *C07C 45/673* (2013.01); *C07C 45/74* (2013.01); *C07C 49/83* (2013.01); *C07D 213/30* (2013.01); *C07D 213/64* (2013.01); *C07D 263/57* (2013.01); *C07D 307/12* (2013.01); *C07D 307/42* (2013.01); *C07D 317/54* (2013.01); *A61K 2800/782* (2013.01)

(58) Field of Classification Search
None
See application file for complete search history.

(56) References Cited

U.S. PATENT DOCUMENTS

| | | | |
|---|---|---|---|
| 4,853,487 A | 8/1989 | Nonn | |
| 6,221,604 B1 | 4/2001 | Upadhya et al. | |
| 2006/0241106 A1 | 10/2006 | Drysdale et al. | |
| 2007/0224301 A1 | 9/2007 | Ribnicky et al. | |
| 2010/0016347 A1* | 1/2010 | Nandy | A23B 7/154 514/277 |

FOREIGN PATENT DOCUMENTS

| | | |
|---|---|---|
| EP | 0443533 | 8/1991 |
| WO | WO9839279 | 9/1998 |

OTHER PUBLICATIONS

Database CAPLUS in STN, Acc. No. 2013:1048031, Reddy Parumala et al., Organic Letters (2013), 15(14), pp. 3546-3549 (abstract).*
Database CAPLUS in STN, Acc. No. 2010:84456, Nandy et al., US 2010/0016347 A1 (Jan. 21, 2010) (abstract).*

(Continued)

*Primary Examiner* — Brian J Davis
(74) *Attorney, Agent, or Firm* — Slater Hersey & Lieberman; Sandra Thompson

(57) ABSTRACT

The present invention is directed to inhibitors of tyrosinase, pharmaceutical compositions comprising such tyrosinase inhibitors, and methods of making and using the same. Specifically, included in the present invention are compositions of matter comprised of at least one 2,4-dihydroxybenzene analog, which inhibit the activity of tyrosinase and which inhibit the overproduction of melanin.

8 Claims, 7 Drawing Sheets

(56) References Cited

OTHER PUBLICATIONS

Database CAPLUS in STN, Acc. No. 2001:45921, Liviero et al., EP 1068864 A1 (Jan. 17, 2001) (abstract).*
Database CAPLUS in STN, Acc. No. 2000:610217, Majumder et al., Journal of the Indian Chemical Society (2000), 77(8), pp. 389-393 (abstract).*
Database CAPLUS in STN, Acc. No. 1998:771697, Dol et al., European Journal of Inorganic Chemistry (1998), 12, pp. 1975-1985 (abstract).*
Database CAPLUS in STN, Acc. No. 1997:505460, Lin et al., Holzforschung (1997), 51(4), pp. 316-324 (abstract).*
Database CAPLUS in STN, Acc. No. 1995:665777, Harms et al., Applied and Environmental Microbiology (1995), 61(7), pp. 2499-2505 (abstract).*
Database CAPLUS in STN, Acc. No. 1994:8276, Sartori et al., Journal of Organic Chemistry (1993), 58(25), pp. 7271-7273 (abstract).*
Database CAPLUS in STN, Acc. No. 1991:631969, Miessner et al., Helvetica Chimica Acta (1991), 74(6), pp. 1205-1212 (abstract).*
Database CAPLUS in STN, Acc. No. 1973:534223, Marchelli et al., Journal of the Chemical Society, Chemical Communications (1973), 15, pp. 555-556 (abstract).*
Database CAPLUS in STN, Acc. No. 1967:464771, Paushkin et al., Vysokomolekulyarnye Soedineniya, Seriya A (1967), 9(6), pp. 1293-1297 (abstract).*
Database CAPLUS in STN, Acc. No. 1992:117371, Shirai et al, JP 03251494 A (Nov. 8, 1991) (abstact).*
Database CAPLUS in STN, Acc. No. 2001:294908, Upadhya et al., U.S. Pat. No. 6,221,604 B1 (Apr. 24, 2001) (abstract).*
Likhitwitayawuid, K., et al., "Chemical transformations of oxyresveratrol (trans-2,4,3',5'-tetrahydroxystilbene) into a potent tyrosinase inhibitor and a strong cytotoxic agent". Bioorganic & Medicinal Chemistry Letters, 2006, vol. 16, pp. 5650-5653.
Govorko, D., et al., "Polyphenolic compounds from *Artemisia dracunculus* L. inhibit PEPCK gene expression and gluconeogenesis in an H4IIE hepatoma cell line". American Journal of Physiology, Endocrinology and Metabolism, 2007, vol. 293, pp. E1503-E1510.
Wang, Y., et al., "Geranyl flavonoids from the leaves of *Artocarpus altilis*". Phytochemistry, 2007, vol. 68, No. 9, pp. 1300-1306.
Forejtnikova, H., et al., "Chemoprotective and toxic potentials of synthetic and natural chalcones and dihydrochalcones in vitro". Toxicology, 2005, vol. 208, No. 1, pp. 81-93.
Wang, Y., et al., "Bioassay-guided Isolation of Antiatherosclerotic Phytochemicals from Artocarpus altilis". Phytotherapy Research, 2006, vol. 20, No. 12, pp. 1052-1055.
Su, B-N., et al., "Activity-guided isolation of the chemical constituents of Muntingia calabura using a quinone reductase induction assay". Phytochemistry, 2003, vol. 63, No. 3, pp. 335-341.
Yao, S-Y., et al., "Chemical constituents of Oxytropis falcate" Zhongguo Zhongyao Zazhi (China Journal of Chinese Materia Medica), Jun. 2008, vol. 33, No. 12, pp. 1418-1421.
Liu, H-B., et al., "Flavonoids with Aldose Reductase Inhibiting Activity: Pharmacophore Modeling and Implications for Mechanism". Wuli Huaxue Xuebao (Acta Phys.-Chim. Sin.), 2007, vol. 23, No. 7, pp. 1059-1064.
Lu, F. and Xu, X-J. "Studies on flavonoids of Oxytropis falcate". Zhongguo Zhongyao Zazhi (China Journal of Chinese Materia Medica), 2007, vol. 32, No. 4, pp. 318-320.
Patent Examination Report No. 1, Australia Patent Office, Oct. 9, 2014.
Tetrahedron Letters, vol. 49, pp. 2469-2471 (published in 2008).

* cited by examiner

SERIES OF SKIN-WHITENING (LIGHTENING) COMPOUNDS

RELATED APPLICATIONS

This application is a continuation of U.S. application Ser. No. 14/154,013, filed Jan. 13, 2014, now allowed, which application is a continuation of U.S. application Ser. No. 13/722,394, filed Dec. 20, 2012, now issued as U.S. Pat. No. 8,658,838, which application is a divisional of U.S. application Ser. No. 12/506,497, filed Jul. 21, 2009, now issued as U.S. Pat. No. 8,362,305, which application claims the benefit of U.S. Provisional Application No. 61/082,422, filed Jul. 21, 2008, which applications are incorporated herein by reference in their entireties.

FIELD OF THE INVENTION

The present invention is directed to novel tyrosinase inhibitors, pharmaceutical, dermatologic and cosmetic compositions comprising such inhibitors, and methods of making and using the same.

BACKGROUND OF THE INVENTION

The color of human skin is determined by the amount and the type of melanin produced by specialized cells, melanocytes, which are located in the basal layers of skin. Melanin, one of the most widely distributed natural pigments, is a homogeneous polyphenol-like biopolymer with a complex structure and color varying from brown to black (eumelanin) and red to yellow (pheomelanin) (Prota G. Med. Res. Rev. 1988, 8, 525-556). In human skin, melanin is believed to act as a protective agent against ultraviolet radiation. As such, people living close to equator have darker skin than those living in areas away from the equator.

Overproduction of melanin can causes different types of abnormal skin color, hair color, and other dermatological disorders, such as melasma, age spots and sites of actinic damage. Melanin is produced through a series of oxidative reactions and polymerization steps starting with the amino acid tyrosine. Tyrosinase (EC1.14.18.1), a type III, copper-containing enzyme catalyzes two initial reactions in the production of melanin: 1) the ortho-hydroxylation of L-tyrosine by monophenolase action, and 2) the oxidation of 3,4-dihydroxyphenylalanine (L-DOPA)→o-dopaquinone by diphenolase action. The later oxidation step is much more rapid than the former, thus, the hydroxylation of tyrosine is considered to be the rate-determining step in melanin biosynthesis. Subsequent conversion of o-dopaquinone to melanin occurs through a series of enzymatic and non-enzymatic polymerization reactions. Other enzymes, such as dopachrome tautomerase (Tyrosinase Related Protein 2; TRP-2) and dihydroxyindole carboxylic acid (DICHA) oxidase (Tyrosinase Related Protein 1; TRP-1) are also involved in the process of the biosynthesis of melanin. Since tyrosinase plays the key role in the process of melanin production, inhibitors of this enzyme are often used as skin-whitening agents (Mosher et al. In Dermatology in General Medicine, 1983, 205-125, Fitzpatrick T. B., Eisen A. Z., Wolff K., Freedberg I. M., Austern K. F. (eds), Mc-Graw-Hill, New York.; Maeda K., Fukuda M, In vitro effectiveness of several whitening cosmetic components in human melanocytes. J. Soc. Cosmet, Chem. 1991, 42, 361-368).

A number of naturally occurring, as well as, synthetic tyrosinase inhibitors have been described in the literature. The majority of compounds comprise a phenol structure. These compounds act as metal chelating agents (Kojima et al. Biol. Pharma. Bull. 1995, 18, 1076-1078.; Seo et al. J. Agric. Food Chem. 2003, 51, 2837-2853.; Fu et al. J. Agric. Food Chem. 2003, 53, 7408-7414.; Kim, Y.-J.; Uyama, H. Cell. Mol. Life Sci. 2005, 62, 1707-1723 and references cited therein). A pharmaceutical product containing hydroquinone (2-4%) is moderately efficacious, but hydroquinone is considered to be cytotoxic to melanocytes and potentially mutagenic to mammalian cells. Unfortunately, several purportedly active agents, e.g., arbutrin and kojic acid, among others have not been demonstrated yet to be clinically efficacious when critically analyzed in carefully controlled studies (Frenk, E. In Melasma: New Approaches to Treatment; Martin Dunitz: London, 1995, 9-15.; Dooley, T. P. In: Drug Discovery Approaches for Developing Cosmeceuticals: Advanced Skin Care and Cosmetic Products; Hori, W., Ed.; International business communications: Southborough, M A, 1997; Dooley, T. P. J. Dermatol. Treat. 1997, 7, 188-200).

Many tyrosinase inhibitors are resorcinol derivatives or polyphenol derivatives of flavonoids or of trans-stilbene, such as resveratrol or its derivatives. These types of compounds are known to form strong chelates with metal ions. (Seo et al. J. Agric. Food Chem. 2003, 51, 2837-2853.; Fu et al. J. Agric. Food Chem. 2003, 53, 7408-7414.; Kim, Y.-J.; Uyama, H. Cell. Mol. Life Sci. 2005, 62, 1707-1723 and references cited therein.; Lerch, K. In: Metal ions in Biological Systems, pp. 143-186; Sigel, H., Ed.; Marcel Dekker, N Y, 1981.; Wilcox et al. In: Substrate analogue binding to the coupled binuclear copper active site in tyrosinase, J. Am. Chem. Soc. 1985, 107, 4015-4027.; Sanchez-Ferrer et al. Biochim. Biophys. Acta 1995, 1247, 1-11.; Decker et al. Angew. Chem. Int. Ed. 2000, 39. 1591-1595.; Decker et al. Angew. Chem. Int. Ed. 2006, 45. 4546-4550.; Briganti et al. Pigment Cell Res. 2003, 16, 101-110). Several compounds based on the resorcinol moiety have been used as tyrosinase inhibitors, see: JP 2008-056651 A; JP 2000-095721 A; US 2005/0267047A1; U.S. Pat. No. 5,339,785; U.S. Pat. No. 6,093,836; US 2008/0032938 A1; U.S. Pat. No. 7,282,592 B2; U.S. Pat. No. 7,339,076 B1; U.S. Pat. No. 5,880,314; U.S. Pat. No. 6,852,310 B2; U.S. Pat. No. 6,077,503; US 2005/0271608 A1; U.S. Pat. No. 5,523,421; US 2007/0098655 A1; US 2005/0267047 A1.

Although many compounds have been reported as potent tyrosinase inhibitors, very few of them have shown skin-whitener properties. Additionally, most of these agents were found either to be toxic, or shown to have adverse side effects in humans. As such, the search for new natural products or synthetic compounds having potent tyrosinase inhibitory activity with low cytotoxicity continues.

SUMMARY OF THE INVENTION

The instant application provides a new series of novel depigmenting agents having excellent inhibitory activity against tyrosinase and very low cytotoxicity. The compounds are stable and easily synthesized from the commonly available starting materials. More specifically, the present invention provides novel 2,4-dihydroxybenzene derivatives, which are useful as tyrosinase inhibitors. The invention encompasses pharmaceutically acceptable salts of these tyrosinase inhibitors. Also encompassed by the invention are pharmaceutical compositions comprised of at least one tyrosinase inhibitor of the invention and at least one pharmaceutically acceptable carrier. The compositions of the present invention can be prepared in any suitable pharmaceutically acceptable dosage form.

The present invention also provides a method for inhibiting the enzyme tyrosinase in a subject in need thereof, said method comprising administering an effective amount of a composition comprising at least one 2,4-dihydroxybenzene tyrosinase inhibitor of the instant invention.

The present invention further provides a method for the prevention and treatment of diseases and conditions related to the activity of the enzyme tyrosinase. The method of prevention and treatment according to this invention comprises administering internally or topically to a subject in need thereof a therapeutically effective amount of at least one novel 2,4-dihydroxybenzene tyrosinase inhibitor of the instant invention.

The present invention also provides a method for inhibiting the synthesis of melanin in a subject in need thereof. Such a method comprises administering an effective amount of a composition comprising at least one 2,4-dihydroxybenzene compound of the instant invention.

The present invention further provides methods for the prevention and treatment of diseases and conditions related to the overproduction or uneven distribution of melanin, said method comprising administering internally or topically to a subject in need thereof a therapeutically effective amount of at least one at least one 2,4-dihydroxybenzene compound of the instant invention. Diseases and conditions related to the overproduction or uneven distribution of melanin include, but not limited to hyper pigmentation spots caused by skin aging, melasma, liver diseases, thermal burns and topical wounds, skin pigmentation due to inflammatory conditions caused by fungal, microbial and viral infections, vitilago, carcinoma, melanoma, as well as other mammalian skin conditions.

The method can also be used for preventing and treating skin darkening and damage resulting from exposure to the sun, ultraviolet (UV) radiation, chemicals, heat, wind and dry environments. Finally, the method can be used for preventing and treating wrinkles, saggy skin, lines and dark circles around the eyes, soothing sensitive skin and preventing and treating dermatitis and other allergy related conditions of the skin.

In specific embodiments, the dose of the 2,4-dihydroxybenzene tyrosinase inhibitor(s) of the instant invention administered to the subject in need thereof is an efficacious, nontoxic quantity generally selected from the range of 0.001% to 100% based on total weight of the final formulation, and/or 0.01 mg to 200 mg per kilogram based on the body weight of the subject. Persons skilled in the art using routine clinical testing are able to determine optimum doses for the particular ailment being treated. The compositions of this invention can be administered by any method known to one of ordinary skill in the art. The modes of administration include, but are not limited to, enteral (oral) administration, parenteral (intravenous, subcutaneous, and intramuscular) administration and topical application. The method of treatment according to this invention comprises administering internally or topically to a patient in need thereof a therapeutically effective amount of at least one 2,4-dihydroxybenzene of the instant invention. In a preferred embodiment the composition is administered topically.

Included in the present invention are novel methods for the synthesis of the 2,4-dihydroxybenzene tyrosinase inhibitor(s) of the invention as described in Examples 1-5. Thus, the present invention provides commercially viable options for the synthesis, and/or isolation, purification and formulation of the 2,4-dihydroxybenzenes of the instant invention to yield a composition of matter having the desirable physiological activity.

In yet another embodiment, the 2,4-dihydroxybenzenes can be used in the food industry to inhibit the browning and color changes in fruits, vegetables, juices and other food products.

Although methods and materials similar or equivalent to those described herein can be used in the practice or testing of the present invention, suitable methods and materials are described below. All publicly available publications, patent applications, patents, and other references mentioned herein are incorporated by reference in their entirety.

It is to be understood that both the foregoing general description and the following detailed description are exemplary and explanatory only and are not restrictive of the invention as claimed. Other objects, advantages, and novel features will be readily apparent to those skilled in the art from the following detailed description.

BRIEF DESCRIPTION OF THE DRAWINGS

FIG. 1 also illustrates graphically cell viability ($LD_{50}$) (x) at varying concentrations of compound 7.

FIG. 2 also illustrates graphically cell viability ($LD_{50}$) (x) at varying concentrations of compound 15. The $LD_{50}$ for compound 15 was determined to be 66 μM.

FIG. 3 also illustrates graphically cell viability ($LD_{50}$) (x) at varying concentrations of compound 16. The $LD_{50}$ for compound 16 was determined to be 260 μM.

FIG. 4 also illustrates graphically cell viability ($LD_{50}$) (x) at varying concentrations of compound 17. The $LD_{50}$ for compound 17 was determined to be 157.8 μM.

FIG. 5 also illustrates graphically cell viability ($LD_{50}$) (x) at varying concentrations of compound 18. The $LD_{50}$ for compound 18 was determined to be 222.2 μM.

FIG. 6 also illustrates graphically cell viability (LD$_{50}$) (x) at varying concentrations of compound 19. The LD$_{50}$ for compound 19 was determined to be 130.3 μM.

FIG. 7 also illustrates graphically cell viability (LD$_{50}$) (x) at varying concentrations of compound 24. The LD$_{50}$ for compound 24 was determined to be 345.9 μM.

FIG. 8 also illustrates graphically cell viability (LD$_{50}$) (x) at varying concentrations of compound 25. The LD$_{50}$ for compound 25 was determined to be >1000 μM.

FIG. 9 also illustrates graphically cell viability (LD 50) (x) at varying concentrations of compound 25. The LD$_{50}$ for compound 30 was determined to be 187.8 μM.

FIG. 10 also illustrates graphically cell viability (LD$_{50}$) (x) at varying concentrations of kojic acid. The LD$_{50}$ for kojic acid was determined to be >1000 μM.

DETAILED DESCRIPTION OF THE PREFERRED EMBODIMENT

Figure 1:
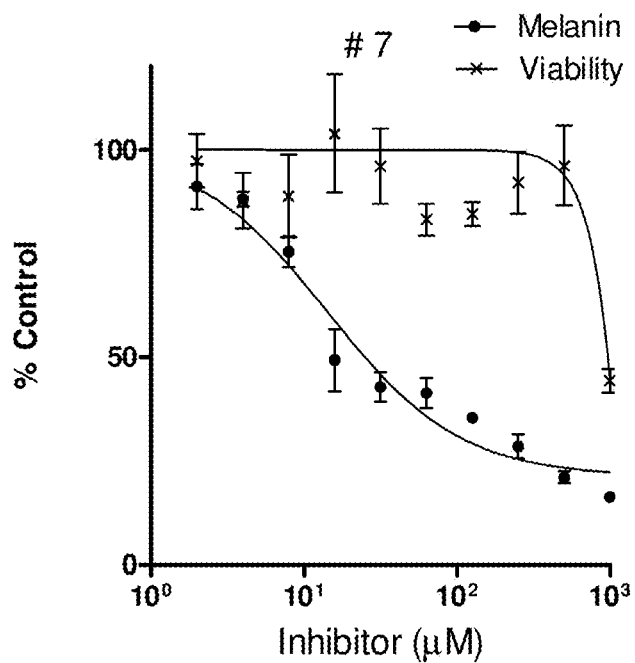
FIG. 1 illustrates graphically a profile of the inhibition in the production of melanin (●) by 4-(pyridin-ylmethyl)benzene-1,3-diol (7) as described in Example 7. The data is presented as melanin content (% of untreated control) vs. inhibitor concentration (μM). The $IC_{50}$ of compound 7 was determined to be 14 μM.
Figure 2:
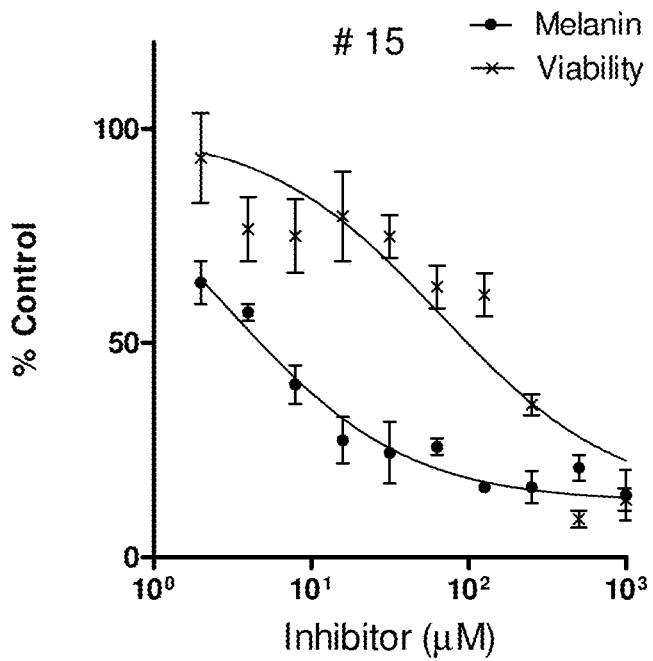
FIG. 2 illustrates graphically a profile of the inhibition in the production of melanin (●) by 4-(2-(benzo[d][1,3]dioxol-5-ylethyl)benzene-1,3-diol (15) as described in Example 7. The data is presented as melanin content (% of untreated control) vs inhibitor concentration (μM). The $IC_{50}$ of compound 15 was determined to be 3.3 μM.
Figure 3:
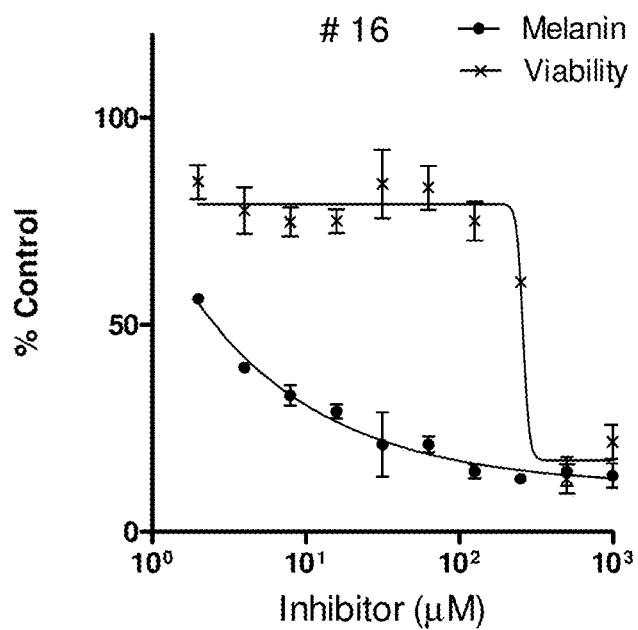
FIG. 3 illustrates graphically a profile of the inhibition in the production of melanin (●) by 4,4'-(ethane-1,2diyl)dibenzene-1,3-diol (16) as described in Example 7. The data is presented as melanin content (% of untreated control) vs. inhibitor concentration (μM). The $IC_{50}$ of compound 16 was determined to be 1.7 μM.
Figure 4:
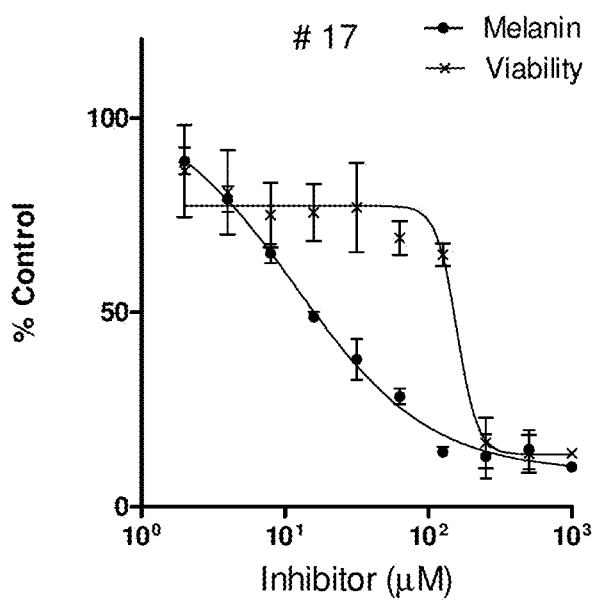
FIG. 4 illustrates graphically a profile of the inhibition in the production of melanin (●) by 4-(2,4-dimethoxyphenethyl)benzene-1,3-diol (17) as described in Example 7. The data is presented as melanin content (% of untreated control) vs inhibitor concentration (μM). The $IC_{50}$ of compound 17 was determined to be 11.9 μM.
Figure 5:
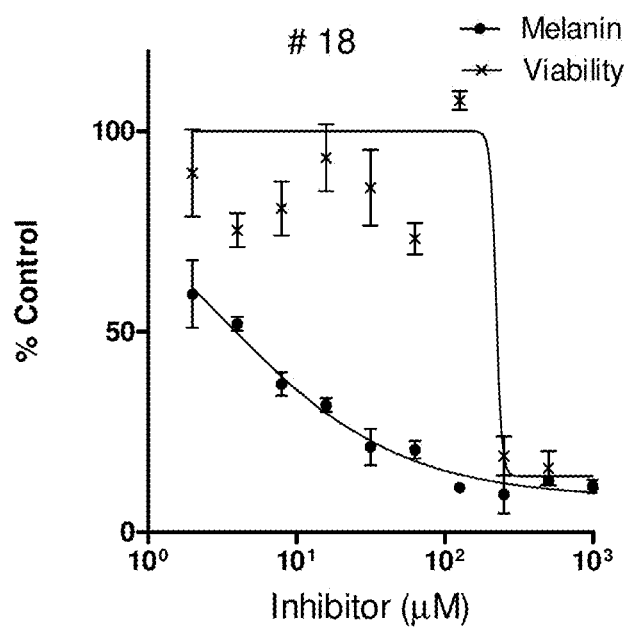
FIG. 5 illustrates graphically a profile of the inhibition in the production of melanin (●) by 4-(3,5-dimethoxyphenethyl)benzene-1,3-diol (18) as described in Example 7. The data is presented as melanin content (% of untreated control) vs inhibitor concentration (μM). The $IC_{50}$ of compound 18 was determined to be 2.97 μM.
Figure 6:
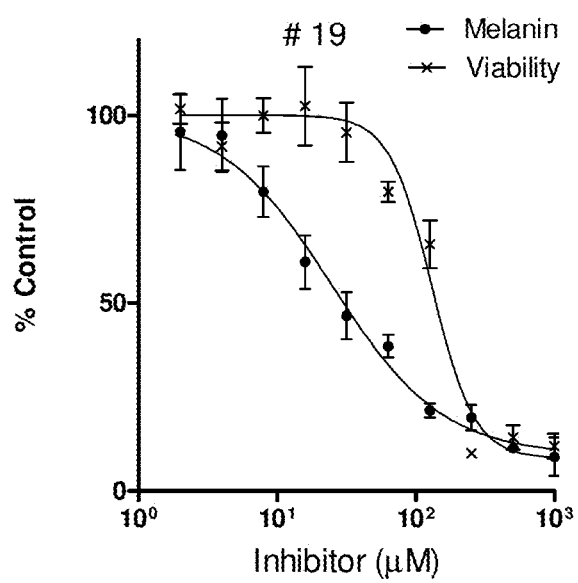
FIG. 6 illustrates graphically a profile of the inhibition in the production of melanin (●) by 4-(2,4-dimethoxy-3-methylphenethyl)benzene-1,3-diol (19) as described in Example 7. The data is presented as melanin content (% of untreated control) vs inhibitor concentration (μM). The IC$_{50}$ of compound 19 was determined to be 24.7 μM.
Figure 7:
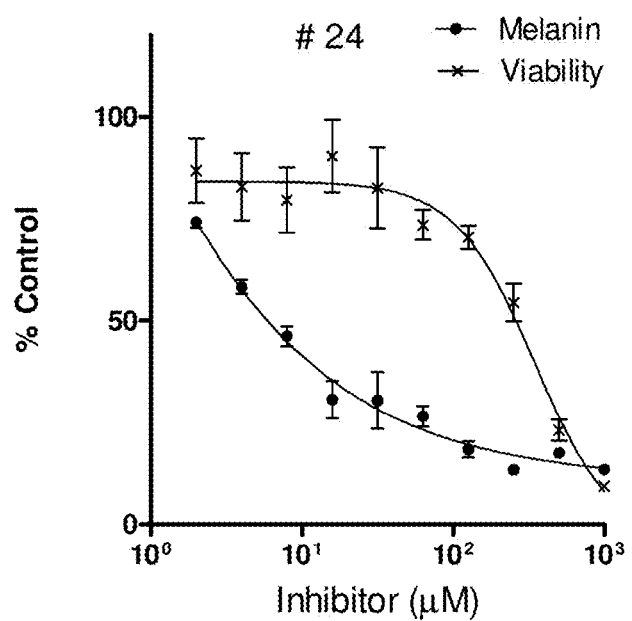
FIG. 7 illustrates graphically a profile of the inhibition in the production of melanin (●) by 4-(2-(furan-2-yl)ethyl) benzene-1,3-diol (24) as described in Example 7. The data is presented as melanin content (% of untreated control) vs. inhibitor concentration (μM). The IC$_{50}$ of compound 24 was determined to be 1.6 μM.
Figure 8:
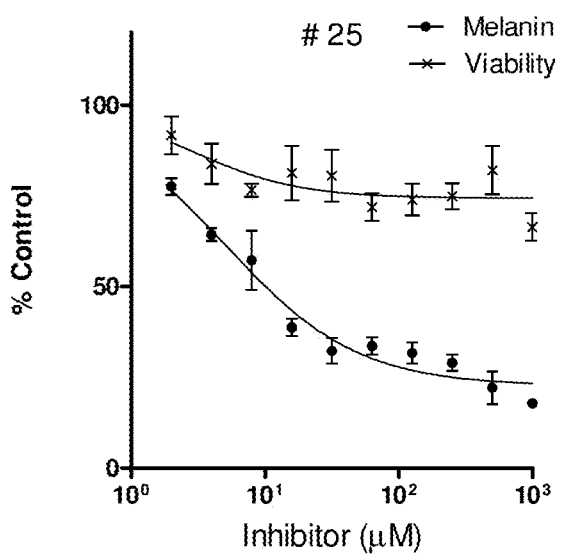
FIG. 8 illustrates graphically a profile of the inhibition in the production of melanin (●) by 4-(2-(tetrahydrofuran-2-yl)ethyl)benzene-1,3-diol (25) as described in Example 7. The data is presented as melanin content (% of untreated control) vs inhibitor concentration (μM). The IC$_{50}$ of compound 25 was determined to be 5 μM.
Figure 9:
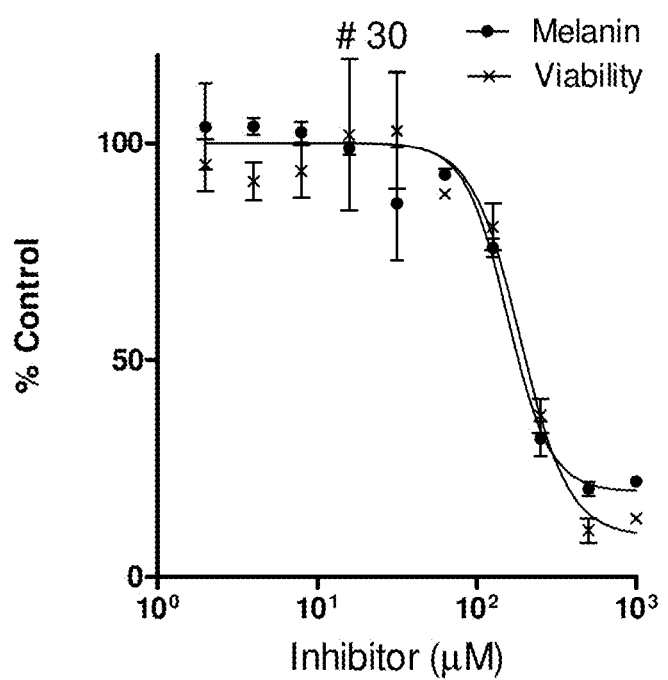
FIG. 9 illustrates graphically a profile of the inhibition in the production of melanin (●) by compound 30 as described in Example 7. The data is presented as melanin content (% of untreated control) vs. inhibitor concentration (μM). The IC$_{50}$ of compound 30 was determined to be 156 μM.

The present disclosure provides pharmaceutical agents that are potent inhibitors of the tyrosinase enzyme. In particular, provided are substituted 2,4-dihydroxybenzene derivatives that are inhibitors of tyrosinase having the structures depicted in Formulas I-IV, below or pharmaceutically acceptable salts thereof

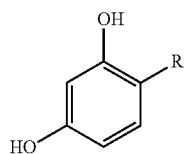

Formula I

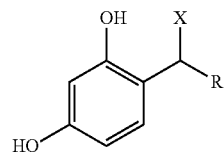

Formula II

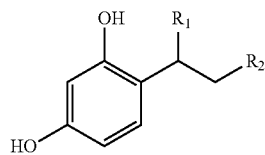

Formula III

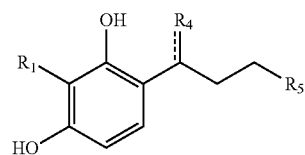

Formula IV

These compounds are shown to have excellent tyrosinase inhibitory activity and low cytotoxicity. Illustrated is the inhibitory activity of representative compounds against mushroom tyrosinase, as well as, the inhibition of melanin production by murine B16-F1 melanoma cells. The skin whitening properties of representative compounds were evaluated by means of a reconstructed human skin model as described in Example 8. These compounds or their pharmaceutically acceptable salts thereof are shown to be useful for both cosmetic and medical applications as detailed below.

As used in this context, the term "derivative" or "analog" refers to a compound having similar chemical structure or function as the compounds of Formula I-IV that retains the core 2,4-dihydroxybenzene ring.

Various terms are used herein to refer to aspects of the present invention. To aid in the clarification of the description of the components of this invention, the following definitions are provided. Unless defined otherwise all technical and scientific terms used herein have the meaning commonly understood by one of ordinary skill in the art to which this invention belongs.

It is to be noted that as used herein the term "a" or "an" entity refers to one or more of that entity; for example, a tyrosinase inhibitor refers to one or more tyrosinase inhibitors. As such, the terms "a" or "an", "one or more" and "at least one" are used interchangeably herein.

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

The term "alkyl" as used herein refers to a straight or branched chain, saturated hydrocarbon having the indicated number of carbon atoms. For example, (C$_1$-C$_{10}$) alkyl is meant to include a straight or branched chain hydrocarbon having one to ten carbon atoms. An alkyl group can be unsubstituted or optionally substituted with one or more substituents as described herein.

The term "alkoxy" as used herein refers to an —O-alkyl group having the indicated number of carbon atoms. For example, a (C$_1$-C$_{10}$) alkoxy group includes —OCH$_3$, —OCH$_2$CH$_3$, etc. up to ten carbon atoms.

As used herein, the term "heteroatom" is meant to include oxygen (O), nitrogen (N) and sulfur (S).

The term "heteroaromatic" as used herein refers to an aromatic heterocyclic ring of 5 to 14 members and having at least one heteroatom selected from nitrogen, oxygen and sulfur, and containing at least 1 carbon atom. Representative heteroaromatics include pyridyl, furyl, thienyl, pyrrolyl and imidazolyl etc. The heteroaryl group can be attached via any heteroatom or carbon atom, where chemically acceptable. A heteroaryl group can be unsubstituted or optionally substituted with one or more substituents as described herein.

As used herein, the term "heterocycle" refers to non-aromatic 5 to 14-membered ring systems which are either saturated, unsaturated and which contain from 1 to 4 heteroatoms independently selected from nitrogen, oxygen and sulfur, and wherein the nitrogen and sulfur heteroatoms can be optionally oxidized, and the nitrogen heteroatom can be optionally quaternized. The heterocycle can be attached via any heteroatom or carbon atom, where chemically acceptable. Representative examples of non-aromatic heterocycles include, but are not limited to tetrahydrofuranyl, tetrahydropyrrolyl, pyranyl and tetrahydropyranyl etc. A heterocycle group can be unsubstituted or optionally substituted with one or more substituents as described herein.

The term "aromatic" as used herein refers to any compound which includes or consists of one or more hydrocarbon aromatic rings. The rings may be mono or polycyclic ring systems. Examples of suitable rings include, but are not limited to benzene, biphenyl, terphenyl, naphthalene etc.

The term "hydroxyalkyl" as used herein, refers to an alkyl group having the indicated number of carbon atoms wherein one or more of the hydrogen atoms in the alkyl group is replaced with an —OH group. Representative examples of hydroxyalkyl groups include, but are not limited to, —CH$_2$OH, —CH$_2$CH$_2$OH, —CH$_2$CH$_2$CH$_2$OH, —CH$_2$CH$_2$CH$_2$CH$_2$CH$_2$OH, —CH$_2$CH$_2$CH$_2$CH$_2$CH$_2$CH$_2$OH, and branched versions thereof. Typically, the hydroxylalkyl is a compound of the formula —(C$_1$-C$_{10}$)alkyl-OH.

"Therapeutic" as used herein, includes prevention, treatment and/or prophylaxis. When used therapeutic refers to humans as well as other animals.

"Pharmaceutically or therapeutically effective dose or amount" refers to a dosage level sufficient to induce a desired biological result. That result may be the alleviation of the signs, symptoms or causes of a disease or any other alteration of a biological system that is desired. The precise dosage will vary according to a variety of factors, including but not limited to the age and size of the subject, the disease and the treatment being effected.

A "host" or "patient" or "subject" is a living mammal, human or animal, for whom therapy is desired. The "host," "patient" or "subject" generally refers to the recipient of the therapy to be practiced according to the method of the invention. It should be noted that the invention described herein may be used for veterinary as well as human applications and that the term "host" should not be construed in a limiting manner. In the case of veterinary applications, the dosage ranges can be determined as described below, taking into account the body weight of the animal.

As used herein, the term "pharmaceutically acceptable" means approved by a regulatory agency of a federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to such sterile liquids as water and oils.

A "pharmaceutically acceptable salt" or "salt" of a tyrosinase inhibitor is a product of the disclosed compound that contains an ionic bond, and is typically produced by reacting the disclosed compound with either an acid or a base, suitable for administering to a subject. A pharmaceutically acceptable salt can include, but is not limited to, acid addition salts including hydrochlorides, hydrobromides, phosphates, sulphates, hydrogen sulphates, alkylsulphonates, arylsulphonates, arylalkylsulfonates, acetates, benzoates, citrates, maleates, fumarates, succinates, lactates, and tartrates; alkali metal cations such as Li, Na, K, alkali earth metal salts such as Mg or Ca, or organic amine salts.

A "pharmaceutical composition" is a formulation comprising the disclosed compounds in a form suitable for administration to a subject. A pharmaceutical composition of the invention is preferably formulated to be compatible with its intended route of administration. Examples of routes of administration include, but are not limited to, oral and parenteral, e.g., intravenous, intradermal, subcutaneous, inhalation, topical, transdermal, transmucosal, and rectal administration.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Examples of substituents include, but are not limited to C$_1$-C$_{10}$ alkyl, hydroxy (—OH); C$_1$-C$_{10}$ alkoxy groups. Typically an aromatic, heteroaromatic or heterocyclic ring will have from 1-3 substituents.

In one of its aspects the present invention provides a compound having a structure shown in Formula I, or a pharmaceutically acceptable salt thereof:

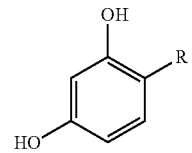

Formula I wherein R is selected from a substituted or unsubstituted aromatic, heteroaromatic or heterocyclic ring. In one embodiment R is selected from the group consisting of a substituted or unsubstituted: phenyl, biphenyl, 2-pyridyl, 3-pyridyl, 4-pyridyl, 2-furanyl, 3-furanyl. In one embodiment R is substituted with 1 to 3 moieties (R', R", R''') independently selected from the group consisting of a C$_1$-C$_{10}$ alkyl group, a C$_1$-C$_{10}$ alkoxy group or a hydroxyl group. In other embodiments R is selected from the group consisting of 1'-(4'-methoxy)phenyl; 1'-(2,4-dihydroxy)phenyl; 1'-(3-pyridyl); 1'-(biphenyl-4-ol).

In one of its aspects the present invention provides a compound having a structure shown in Formula II or a pharmaceutically acceptable salt thereof

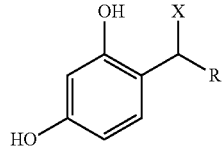

Formula II wherein X=H or —OH and R is selected from a substituted or unsubstituted aromatic, heteroaromatic or heterocyclic ring. In one embodiment R is selected from the group consisting of a substituted or unsubstituted: phenyl, biphenyl, 2-pyridyl, 3-pyridyl, 4-pyridyl, 2-furanyl, 3-furanyl. In one embodiment, R is substituted with 1 to 3 moieties (R', R'', R''') independently selected from the group consisting of a $C_1$-$C_{10}$ alkyl group, a $C_1$-$C_{10}$ alkoxy group or a hydroxyl group. In other embodiments R is selected from the group consisting of 2'-furyl; 3'-furyl; 3'-pyridyl; 3'-(2-methoxypyridyl); 1'-(2,4,6-trimethoxy phenyl); 1'-(3,4-dioxalane phenyl) and when X=OH, R is 3'-pyridyl.

In one of its aspects the present invention provides a compound having a structure shown in Formula III or a pharmaceutically acceptable salt thereof.

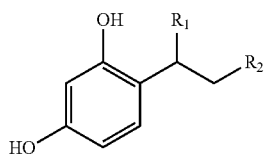

Formula III wherein $R_1$ is selected from the group consisting of H, or $C_1$-$C_{10}$ alkyl; and $R_2$ is selected from a substituted or unsubstituted: aromatic ring, heteroaromatic ring or heterocyclic ring. In particular embodiments $R_1$ is selected from H or —$CH_3$ and $R_2$ is selected from a substituted or unsubstituted: aromatic ring, heteroaromatic ring or heterocyclic ring. In yet other embodiments, $R_2$ is substituted with 1 to 3 moieties (R', R'', R''') independently selected from the group consisting of a $C_1$-$C_{10}$ alkyl group, a $C_1$-$C_{10}$ alkoxy group or a hydroxyl group. In other embodiments $R_2$ is selected from the group consisting of a substituted or unsubstituted: phenyl, biphenyl, 2-pyridyl, 3-pyridyl, 4-pyridyl, 2-furanyl, 3-furanyl or 2-tetrahydrofuranyl. In specific embodiments $R_2$ is selected from the group consisting of $R_1$ is H and $R_2$ is 1'-phenyl; 1'-(4-hydroxyphenyl); 1'-(4-methoxyphenyl); 1'-(3,4-dioxalane)phenyl; 1'-(2,4-dihydroxyphenyl); 1'-(2,4-dimethoxyphenyl); 1'-(3,5-dimethoxyphenyl); 1'-(2,4-dimethoxy-3-methylphenyl); 1'-(2,4,6-trimethoxyphenyl); 3-furyl; 3-tetrahydrofuryl; 2'-furyl, 2'-tetrahydrofuryl; 2'-(5'-ethyl)-furyl; 3'-pyridyl and also $R^1$=Me, $R_2$=1'-phenyl In one of its embodiments the present invention provides a compound having a structure shown in Formula II or a pharmaceutically acceptable salt thereof

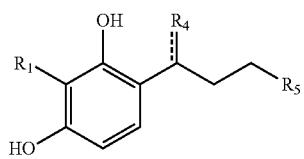

Formula IV wherein === represents double or single bond,
$R_1$ is selected from the group consisting of H or $C_1$-$C_{10}$ alkyl;
$R_4$ is selected from the group consisting of =H, OH or O; and
$R_5$ is a selected from the group consisting of a substituted or unsubstituted: aromatic ring, heteroaromatic ring, heterocyclic ring or a hydroxylalkyl moiety. In specific embodiments $R_1$ is H or $CH_3$ and $R_5$ is selected from a substituted or unsubstituted: aromatic ring, heteroaromatic ring or a heterocyclic ring or a $C_1$-$C_{10}$ hydroxylalkyl (—$C_1$-$C_{10}$)—OH). In yet other embodiments, $R_5$ is substituted with 1 to 3 moieties (R', R'', R''') independently selected from the group consisting of a $C_1$-$C_{10}$ alkyl group, a $C_1$-$C_{10}$ alkoxy group or a hydroxyl group. In other embodiments $R_5$ is selected from the group consisting of a substituted or unsubstituted: phenyl, biphenyl, 2-pyridyl, 3-pyridyl, 4-pyridyl, 2-furanyl, 3-furanyl or 2-tetrahydrofuranyl. In specific embodiments $R_1$=$R_4$=H and $R_5$ is selected from 1'-(3',5'-dimethoxy)phenyl; 1'-(3',5'-dihydroxy)phenyl; 1-(2',4',6-trimethoxyphenyl); $R_1$=Me, $R_4$=OH, $R_5$ is 1'-(2',4'-dihydroxy)phenyl; $R_1$=Me, $R_4$=0, $R_5$ is 1'-(2',4'-dihydroxy)phenyl; and $R_1$=$R_4$=H, $R_5$, —$CH_2CH_2OH$.
with the following provisos:
proviso 1: when $R_1$=$R_4$=H; $R_5$ cannot be 1'-(2,4-dimethoxy-3-methyl)phenyl.
proviso 2: when $R_1$=$R_4$=H; $R_5$ cannot be 1'-(2,4-dihydroxy)phenyl; 1'-(2,4-dialkoxy)phenyl; 1'-(2,4-dialkenoxy)phenyl or 1'-(2,4-dibenzyloxy)phenyl.
proviso 3: $R_5$ cannot be 1'-(4-hydroxy)phenyl.
proviso 4: when $R_1$=$R_4$=H; $R_5$ cannot be 1'-(2,4-di(CO)$R^1$, wherein $R^1$ is a ($C_1$-$C_{20}$)-alkyl group.
proviso 5: when $R_1$=$R_4$=H and $R_5$ cannot be a 1'-(2,4-disubstituted)phenyl; wherein said substituents are selected from —$OR^2$ and —$OR^3$, wherein $R^2$ and $R^3$ are independently selected from the group consisting of H or a ($C_1$-$C_{20}$)-alkyl.
proviso 6: when $R_1$=H and $R_4$=OH; $R_5$ cannot be 1'-(3,4-dihydroxy)phenyl; 1'-(3,4-dimethoxy)phenyl; 1'-(2-hydroxy)phenyl; 1'-(2-methoxy)phenyl; 1'-(4-methoxy)phenyl; phenyl; 1'-(3-methoxy,4-hydroxy)phenyl.

Table 1 lists representative novel 2,4-dihydroxybenzene analogs of Formula I which are useful as tyrosinase inhibitors. The synthetic methods that can be used to prepare each compound, identified in Table 1 are described in detail in Example 1. Supporting $^1H$- and $^{13}C$-NMR data is provided for each compound synthesized. In general, the compounds of Formula I can be synthesized from readily available materials using standard organic synthesis techniques. Further preparation routes may be found in the literature and relevant art. $IC_{50}$ values for these compounds as determined by the tyrosinase assay as described in Example 6 are also set forth in Table 1. For select compounds of Formula I, Table 5 provides $IC_{50}$ values as determined by the murine melanoma cell-based assays described in Example 7 and cell viability ($LD_{50}$) as determined by the methods described in Example 8.

Table 2 lists representative novel 2,4-dihydroxybenzene derivatives of Formula II which are useful as tyrosinase inhibitors. The synthetic methods that can be used to prepare each compound identified in Table 2 are described in detail in Example 2. Supporting $^1H$- and $^{13}C$-NMR data is provided for each compound synthesized. In general, the compounds of Formula II can be synthesized from readily available materials using standard organic synthesis techniques. Further preparation routes may be found in the literature and relevant art. $IC_{50}$ values for these compounds as determined by the tyrosinase assay as described in Example 6 are also set forth in Table 2. For select compounds of Formula II, Table 5 provides $IC_{50}$ values as determined by the murine melanoma cell-based assay described in Example 7 and cell viability ($LD_{50}$) as determined by the methods described in Example 8.

Table 3 lists representative novel 2,4-dihydroxybenzene analogs of Formula III which are useful as tyrosinase inhibitors. The synthetic methods that can be used to prepare each compound identified in Table 3 are described in detail in Example 3. Supporting $^1$H- and $^{13}$C-NMR data is provided for each compound synthesized. In general, the compounds of Formula III can be synthesized from readily available materials using standard organic synthesis techniques. Further preparation routes may be found in the literature and relevant art. $IC_{50}$ values for these compounds as determined by the tyrosinase assay as described in Example 6 are also set forth in Table 3. For select compounds of Formula III, Table 5 provides $IC_{50}$ values as determined by the murine melanoma cell-based assay described in Example 7 and cell viability ($LD_{50}$) as determined by the methods described in Example 8.

Table 4 lists representative novel 2,4-dihydroxybenzene analogs of Formula IV which are useful as tyrosinase inhibitors. The synthetic methods that can be used to prepare each compound identified in Table 4 are described in detail in Example 4 and Example 5 (compound 34). Supporting $^1$H- and $^{13}$C-NMR data is provided for each compound synthesized. In general, the compounds of Formula IV can be synthesized from readily available materials using standard organic synthesis techniques. Further preparation routes may be found in the literature and relevant art. $IC_{50}$ values for these compounds as determined by the tyrosinase assay as described in Example 6 are also set forth in Table 4. For select compounds of Formula IV, Table 5 provides $IC_{50}$ values as determined by the murine melanoma cell-based assay described in Example 7 and cell viability ($LD_{50}$) as determined by the methods described in Example 8.

Figure 10:
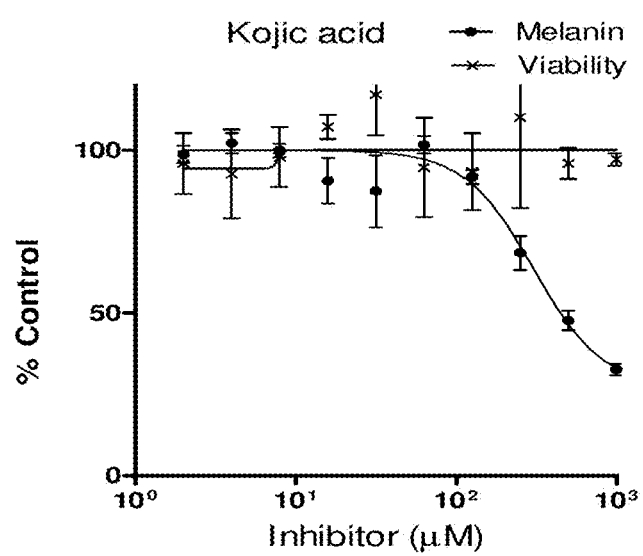
FIG. 10 illustrates graphically a profile of the inhibition in the production of melanin (●) by kojic acid as described in Example 7. The data is presented as melanin content (% of untreated control) vs inhibitor concentration (μM). The IC$_{50}$ of kojic acid in the murine assay was determined to be 303.5 μM.
Figure 11A:
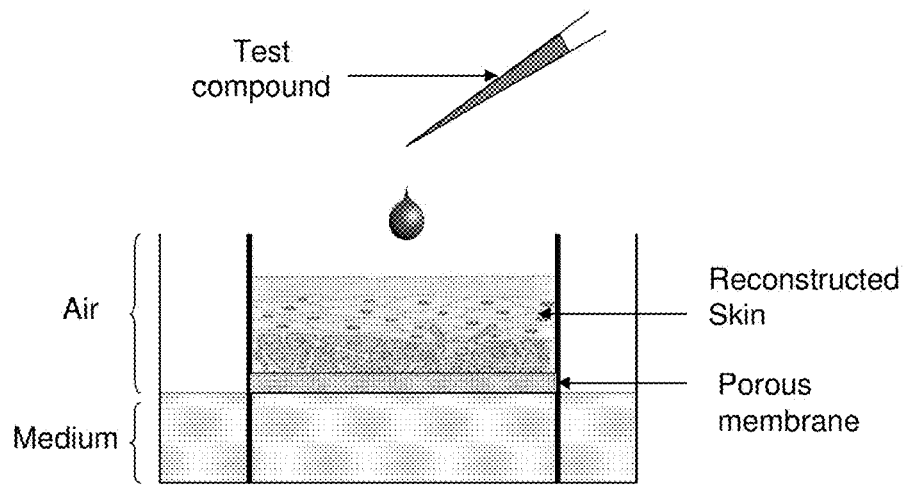
FIG. 11A depicts the reconstructed skin prepared as described in Example 8. The reconstructed skin was grown at the air-liquid interface, making it possible to mimic topical application of skin whitening agents.
Figure 11B:
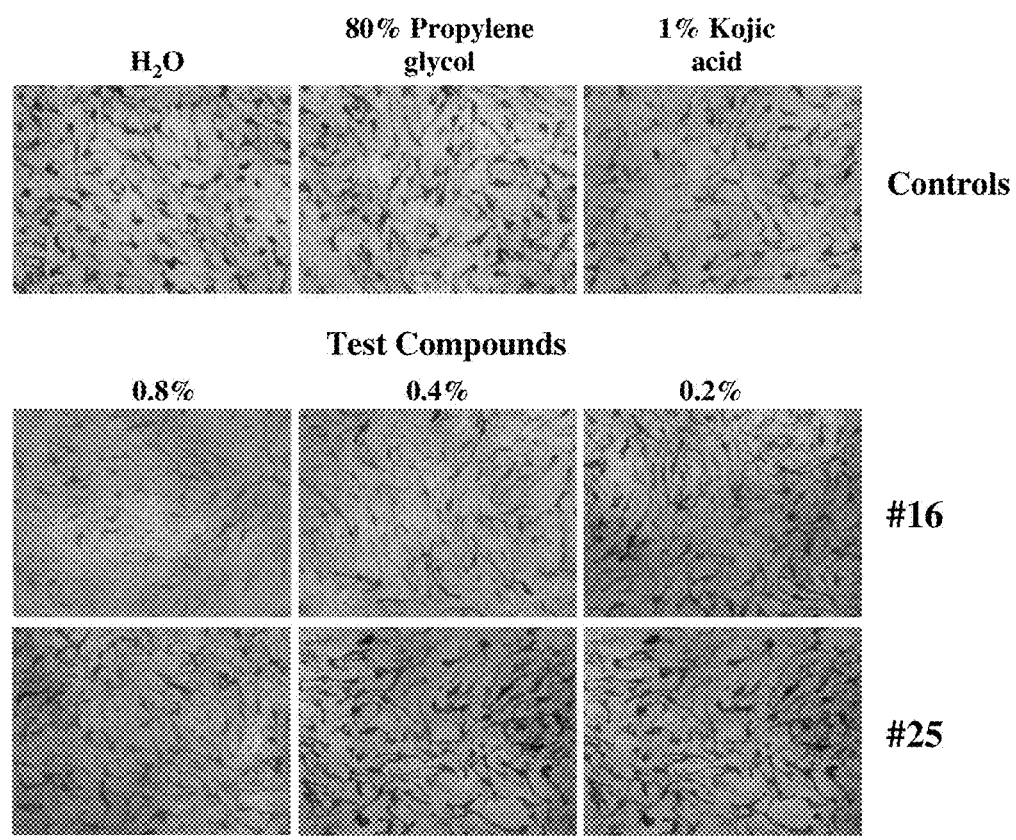
FIG. 11B depicts photographically the results of the reconstructed skin studies as described in Example 8. Photographs of skin specimen taken after 15 days of the experiment show significant dose-dependent whitening effects on melanocytes, which appear on photographs as dark dendritic cells.

In summary, the compounds set forth shown in Tables 1-4 exhibited excellent inhibition of the mushroom tyrosinase enzyme, as well as, melanin production by B16-F1 cells (Table 5, FIGS. 1-9). Cytotoxicity was observed only at high concentrations. All compounds exemplified in Table 5 (i.e., compounds 7, 15, 16, 17, 18, 19, 24, 25, 30) were much more potent than kojic acid, a commonly used skin whitener as illustrated in FIG. 10. The $IC_{50}$ of kojic acid (tyrosinase assay) is 20 µM. The $IC_{50}$ of kojic acid (murine assay) is 303.5 µM. Additionally, two of the compounds tested (compounds 16 and 25) exhibited strong skin-whitening effects in a reconstructed skin model without any detectable cytotoxicity as described in Example 8.

The present invention encompasses pharmaceutical compositions comprising at least one tyrosinase inhibitor described herein. The compositions of the present invention can be formulated as pharmaceutical compositions, which include other components such as a pharmaceutically and/or cosmetically acceptable excipient, an adjuvant, and/or a carrier. For example, compositions of the present invention can be formulated in an excipient that the host to be treated can tolerate. An excipient is an inert substance used as a diluent or vehicle for a therapeutic agent. Examples of such excipients include, but are not limited to water, buffers, saline, Ringer's solution, dextrose solution, mannitol, Hank's solution, preservatives and other aqueous physiologically balanced salt solutions. Nonaqueous vehicles, such as fixed oils, sesame oil, ethyl oleate, or triglycerides may also be used. Other useful formulations include suspensions containing viscosity-enhancing agents, such as sodium carboxymethylcellulose, sorbitol or dextran. Excipients can also contain minor amounts of additives, such as substances that enhance isotonicity and chemical stability. Examples of buffers include phosphate buffer, bicarbonate buffer, tris buffer, histidine, citrate, and glycine, or mixtures thereof, while examples of preservatives include, but are not limited to EDTA, disodium EDTA, BHA, BHT, vitamin C, vitamin E, sodium bisulfite, $SnCl_2$, thimerosal, m- or o-cresol, formalin and benzyl alcohol. Standard formulations can be either liquid or solids, which can be taken up in a suitable liquid as a suspension or solution for administration. Thus, in a non-liquid formulation, the excipient can comprise dextrose, human serum albumin, preservatives, etc., to which sterile water or saline can be added prior to administration.

In one embodiment of the present invention, the composition can also include an adjuvant or a carrier. Adjuvants are typically substances that generally enhance the biological response of a host to a specific bioactive agent. Suitable adjuvants include, but are not limited to, Freund's adjuvant, other bacterial cell wall components, aluminum, magnesium, copper, zinc, iron, calcium, and other metal ion based salts, silica, polynucleotides, toxoids, serum proteins, viral coat proteins, other bacterial-derived preparations, gamma interferon; block copolymer adjuvants; such as Hunter's Titermax adjuvant (Vaxcel™, Inc. Norcross, Ga.), Ribi adjuvants (available from Ribi ImmunoChem Research, Inc., Hamilton, Mont.); and saponins and their derivatives, such as Quil A (available from Superfos Biosector A/S, Denmark). Carriers are typically compounds that increase the half-life of a therapeutic composition in the treated host. Suitable carriers include, but are not limited to, polymeric controlled release formulations, biodegradable implants, liposomes, bacteria, viruses, oils, esters, and glycols. Suitable carriers are described in "Remington: The Science and Practice, Twentieth Edition," published by Lippincott Williams & Wilkins, which is incorporated herein by reference.

In one embodiment, the composition is prepared as a controlled release formulation, which slowly releases the composition of the present invention into the host. As used herein, a controlled release formulation comprises a composition of the present invention in a controlled release vehicle. Suitable controlled release vehicles will be known to those skilled in the art. Preferred controlled release formulations are biodegradable (i.e., bioerodible).

The compositions of this invention can be administered by any method known to one of ordinary skill in the art. The modes of administration include, but are not limited to, enteral (oral) administration, parenteral (intravenous, subcutaneous, and intramuscular) administration and topical application. The method of treatment according to this invention comprises administering internally or topically to a patient in need thereof a therapeutically effective amount of at least one of the 2,4-dihydroxybenzene analogs of the instant invention.

In one embodiment, the therapeutic agents of the instant invention are administered topically by any suitable means, known to those of skill in the art for topically administering therapeutic compositions including, but not limited to as an ointment, gel, lotion, or cream base, or as a toothpaste, mouth-wash, or coated on dental flossing materials or as an emulsion, as a patch, dressing or mask, a nonsticking gauze, a bandage, a swab or a cloth wipe.

A therapeutic composition can be administered in a variety of unit dosage forms depending upon the method of administration. For particular modes of delivery, a therapeutic composition of the present invention can be formulated in an excipient of the present invention. A therapeutic reagent of the present invention can be administered to any host, preferably to mammals, and more preferably to humans. The particular mode of administration will depend on the condition to be treated.

In one embodiment, a suitable ointment is comprised of the desired concentration of at least one 2,4-dihydroxybenzene analog of the instant invention, that is an efficacious, nontoxic quantity generally selected from the range of 0.001% to 100% based on the total weight of the topical formulation, from 65 to 100% (preferably 75 to 96%) of white soft paraffin, from 0 to 15% of liquid paraffin, and from 0 to 7% (preferably 3 to 7%) of lanolin or a derivative or synthetic equivalent thereof. In another embodiment the ointment may comprise a polyethylene-liquid paraffin matrix.

In one embodiment, a suitable cream is comprised of an emulsifying system together with the desired concentration of at least one 2,4-dihydroxybenzene analog of the instant invention as provided above. The emulsifying system is preferably comprised of from 2 to 10% of polyoxyethylene alcohols (e.g. the mixture available under the trademark Cetomacrogol™1000), from 10 to 25% of stearyl alcohol, from 20 to 60% of liquid paraffin, and from 10 to 65% of water; together with one or more preservatives, for example from 0.1 to 1% of N,N"-methylenebis[N'-[3-(hydroxymethyl)-2,5-dioxo-4-imidazolidinyl]urea] (available under the name Imidurea USNF), from 0.1 to 1% of alkyl 4-hydroxybenzoates (for example the mixture available from Nipa Laboratories under the trade mark Nipastat), from 0.01 to 0.1% of sodium butyl 4-hydroxybenzoate (available from Nipa Laboratories under the trade mark Nipabutyl sodium), and from 0.1 to 2% of phenoxyethanol.

In one embodiment, a suitable gel is comprised of a semi-solid system in which a liquid phase is constrained within a three dimensional polymeric matrix with a high degree of cross-linking. The liquid phase may be comprised of water, together with the desired amount of at least one 2,4-dihydroxybenzene analog of the instant invention, from 0 to 20% of water-miscible additives, for example glycerol, polyethylene glycol, or propylene glycol, and from 0.1 to 10%, preferably from 0.5 to 2%, of a thickening agent, which may be a natural product, selected from the group including, but not limited to tragacanth, pectin, carrageen, agar and alginic acid, or a synthetic or semi-synthetic compound, selected from the group including, but not limited to methylcellulose and carboxypolymethylene (carbopol); together with one or more preservatives, selected from the group including, but not limited to for example from 0.1 to 2% of methyl 4-hydroxybenzoate (methyl paraben) or phenoxyethanol-differential. Another suitable base, is comprised of the desired amount of at least one 2,4-dihydroxybenzene analog of the instant invention, together with from 70 to 90% of polyethylene glycol (for example, polyethylene glycol ointment containing 40% of polyethylene glycol 3350 and 60% of polyethylene glycol 400, prepared in accordance with the U.S. National Formulary (USNF)), from 5 to 20% of water, from 0.02 to 0.25% of an anti-oxidant (for example butylated hydroxytoluene), and from 0.005 to 0.1% of a chelating agent (for example ethylenediamine tetraacetic acid (EDTA)).

The term soft paraffin as used above encompasses the cream or ointment bases white soft paraffin and yellow soft paraffin. The term lanolin encompasses native wool fat and purified wool fat. Derivatives of lanolin include in particular lanolins which have been chemically modified in order to alter their physical or chemical properties and synthetic equivalents of lanolin include in particular synthetic or semisynthetic compounds and mixtures which are known and used in the pharmaceutical and cosmetic arts as alternatives to lanolin and may, for example, be referred to as lanolin substitutes.

One suitable synthetic equivalent of lanolin that may be used is the material available under the trademark Softisan™ known as Softisan 649. Softisan 649, available from Dynamit Nobel Aktiengesellschaft, is a glycerine ester of natural vegetable fatty acids, of isostearic acid and of adipic acid; its properties are discussed by H. Hermsdorf in Fette, Seifen, Anstrichmittel, Issue No. 84, No. 3 (1982), pp. 3-6.

The other substances mentioned hereinabove as constituents of suitable ointment or cream bases and their properties are discussed in standard reference works, for example pharmacopoeia. Cetomacrogol 1000 has the formula $CH_3(CH_2)_m(OCH_2CH_2)$—OH, wherein m may be 15 or 17 and n may be 20 to 24. Butylated hydroxytoluene is 2,6-di-tert-butyl-p-cresol. Nipastat is a mixture of methyl, ethyl, propyl and butyl 4-hydroxybenzoates.

The compositions of the invention may be produced by conventional pharmaceutical techniques. Thus the aforementioned compositions, for example, may conveniently be prepared by mixing together at an elevated temperature, preferably 60-70° C., the soft paraffin, liquid paraffin if present, and lanolin or derivative or synthetic equivalent thereof. The mixture may then be cooled to room temperature, and, after addition of the hydrated crystalline calcium salt of mupirocin, together with the corticosteroid and any other ingredients, stirred to ensure adequate dispersion.

Regardless of the manner of administration, the specific dose is calculated according to the approximate body weight of the host. Further refinement of the calculations necessary to determine the appropriate dosage for treatment involving each of the above mentioned formulations is routinely made by those of ordinary skill in the art and is within the scope of tasks routinely performed by them without undue experimentation, especially in light of the dosage information and assays disclosed herein. These dosages may be ascertained through use of the established assays for determining dosages utilized in conjunction with appropriate dose-response data.

The tyrosinase inhibitors of the invention can readily be synthesized using known synthetic methodologies or via a modification of known synthetic methodologies. As would be readily recognized by a skilled artisan, the methodologies described below allow the synthesis of 2,4-dihydroxybenzene analogs having a variety of substituents. Included in this invention is a method of synthesizing the 2,4-dihydroxybenzen analogs described herein. Exemplary synthetic methods are described in Examples 1-5 below.

The invention encompasses methods of preventing or treating (e.g., alleviating one or more symptoms of) medical conditions through use of one or more of the disclosed compounds. The methods of preventing or treating comprise administering a therapeutically effective amount of at least one tyrosinase inhibitor of the instant invention to a patient in need thereof. The compositions of the invention can also be used for prophylactic therapy.

The present invention provides a method of treating a subject afflicted with a disorder ameliorated by the inhibition of the activity tyrosinase or the production of excess amounts of melanin. Such a method comprises administering to a subject a therapeutically effective amount of a tyrosinase inhibitor as described herein.

As used herein, "treating" describes the management and care of a patient for the purpose of combating a disease, condition, or disorder and includes the administration of a compound of the present invention to prevent the onset of the symptoms or complications, alleviating the symptoms or complications, or eliminating the disease, condition or disorder. More specifically, "treating" includes reversing, alleviating, minimizing, suppressing or halting at least one deleterious symptom or effect of a disease (disorder) state, disease progression, or other abnormal condition. Treatment is continued as long as symptoms and/or pathology ameliorate.

More specifically the present invention also provides a method for inhibiting the synthesis of melanin in a subject in need thereof. Such a method comprises administering an effective amount of a composition comprising at least one of the 2,4-dihydroxybenzene analogs of the instant invention.

The present invention further provides methods for the prevention and treatment of diseases and conditions related to the overproduction or uneven distribution of melanin, said method comprising administering internally or topically to a subject in need thereof a therapeutically effective amount of at least one at least one 2,4-dihydroxybenzene compound of the instant invention. Diseases and conditions related to the overproduction or uneven distribution of melanin include, but not limited to hyperpigmentation spots caused by skin aging, melasma, liver diseases, thermal burns and topical wounds, skin pigmentation due to inflammatory conditions caused by fungal, microbial and viral infections, vitilago, carcinoma, melanoma, as well as other mammalian skin conditions.

The method can also be used for preventing and treating skin darkening and damage resulting from exposure to the sun, ultraviolet (UV) radiation, chemicals, heat, wind and dry environments. Finally, the method can be used for preventing and treating wrinkles, saggy skin, lines and dark circles around the eyes, soothing sensitive skin and preventing and treating dermatitis and other allergy related conditions of the skin.

In addition to their use for the prevention and treatment of the above described diseases and conditions of the skin, the therapeutic compositions described herein provide an efficacious composition that yields the benefit of smooth and youthful skin appearance with improved skin color, enhanced elasticity, reduced and delayed aging, enhanced youthful appearance and texture, and increased flexibility, firmness, smoothness and suppleness.

In yet another embodiment, the 2,4-dihydroxybenzene derivatives of the instant invention can be used in the food industry to inhibit the browning and color changes in fruits, vegetables, juices and other food products.

The following examples are given to illustrate the present invention. It should be understood, however, that the invention is not to be limited to the specific conditions or details described in these examples. Throughout the specification, any and all references to a publicly available document, including a U.S. patent, are specifically incorporated by reference.

EXAMPLES

Example 1. General and Specific Methods for the Synthesis of Compounds of Formula I

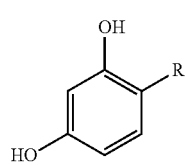

Formula I

Compounds of Formula I were prepared generally as set forth in Scheme 1, using a substituted bromobenzene as R for purposes of illustration. Briefly, the biphenyl compounds of Formula I were prepared by Kumada coupling reaction (Tamao, K.; Sumitani, K.; Kumada, M, *Journal of the American Chemical Society.* 1972, 94. 4374-4376) using Ni(dppp)Cl$_2$ catalyst from the corresponding Grignard reagents with appropriate aryl bromide followed by reductive debenzylation reaction of benzyl group.

Scheme 1

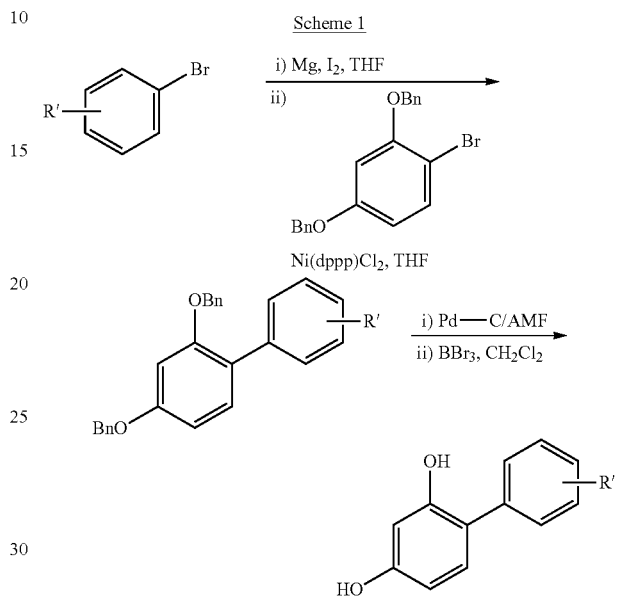

Representative Procedure for Scheme 1: Synthesis of 4'-Methoxybiphenyl-2,4-diol (1)

4-Bromoanisole (2.80 g, 15 mmol) was treated with magnesium turnings (480 mg, 20 mmol) and iodine (a pinch) in THF to make the corresponding Grignard reagent. The Grignard reagent was then added to a stirred solution of benzyl protected 4-bromoresorcinol (3.7 g, 10 mmol) and Ni(dppp)Cl$_2$ (2.7 g, 5 mmol) in THF at 0° C. The reaction mixture was allowed to stir at room temperature for 30 minutes after which it was heated to reflux for 4 h. The reaction mixture was then cooled down and quenched with ammonium chloride, extracted with ethyl acetate, washed with brine and dried over anhydrous Na$_2$SO$_4$, filtered and concentrated in rotary evaporator and purified by column chromatography to yield (1.98 g, 50%) of the coupled product as an off white solid.

The resulting coupled product (1.5 g, 3.7 mmol) was then treated with a catalytic amount of 10% Pd on activated carbon (150 mg) and an excess amount of ammonium formate (1.9 g, 29.6 mmol) in 15 mL THF/MeOH (1:2) solution at reflux for 3 h to remove the benzyl protection group. After filtration through Celite to remove the catalyst, the crude product was purified by column chromatography to yield (720 mg, 90%) of compound 1 as an off-white solid. $^1$H-NMR (MeOD, 500 MHz): δ 7.152 (d, 2H, J=8.5 Hz), 6.718-6.762 (m, 3H), 6.443 (d, 1H, J=2.5 Hz), 6.241 (dd, 1H, J=2.5 & 8.0 Hz), 3.663 (s, 3H).

Representative compounds 2-4 of Formula I (see Table 1) were synthesized according to the same protocol using appropriate staring materials. Overall yields varied from 40-50%.

Biphenyl-2,2',4,4'-tetraol (2)

$^1$H-NMR (MeOD, 300 MHz): δ 7.007-6.953 (m, 2H), 6.378-6.327 (m, 6H). $^{13}$C-NMR (MeOD, 75 MHz): δ 157.971 (6C), 130.246 (2CH), 107.134 (2CH), 102.589 (2CH).

4-(Pyridin-3yl)benzene-1,3-diol (3)

$^1$H-NMR: (CDCl$_3$, 300 MHz): δ 8.829 (s, 1H), 8.539 (d, 1H, J=3.6 Hz), 7.885 (d, 1H, J=7.5 Hz), 7.605-7.261 (m, 1H), 6.753 (s, 1H), 6.711 (d, 1H, J=8.4 Hz). $^{13}$C-NMR (CDCl$_3$, 75 MHz): δ 157.036 (C), 150.534 (CH), 137.420 (CH), 136.926 (CH), 134.400 (C), 131.618 (CH), 129.237 (C), 127.931 (CH), 120.872 (C), 106.821 (CH), 101.769 (CH).

4-(4'-Hydroxybiphenyl)benzene-1,3-diol (4)

$^1$H-NMR (MeOD, 300 MHz): δ 7.511-7.183 (m, 9H), 6.88-6.83 (m, 2H). $^{13}$C-NMR (MeOD, 75 MHz): δ 156.949 (3C), 141.204 (2C), 132.709 (2C), 128.557 (2CH), 127.893 (3 CH), 126.256 (3CH), 115.472 (3 CH).

Example 2. General and Specific Methods for the Synthesis of Compounds of Formula II

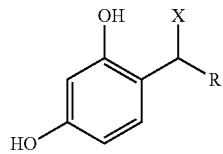

Formula II

Compounds of Formula II were prepared as illustrated in Scheme 2. Briefly, with reference to Scheme 2, the diphenylmethane compounds illustrative of Formula II were prepared by Grignard addition reaction with an aldehyde (RCHO, wherein R=aromatic or heteroaromatic ring), followed by dehydroxylation of resulting benzylic hydroxyl group and debenzylation of benzyloxy protecting groups in situ.

TABLE 1

Compounds Representative of Formula I

| Compound | Structure | Mushroom Tyrosinase Assay |
|---|---|---|
| 4'-Methoxybiphenyl-2,4-diol (1) | 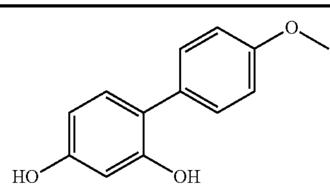 | IC$_{50}$: = 12.8 µM |
| Biphenyl-2,2',4,4'-tetraol (2) | 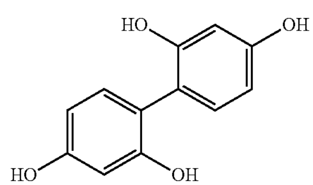 [SMILES: Oc1ccc(-c2ccc(O)cc2O)c(O)c1] | IC$_{50}$: = 60.0 µM |
| 4-(Pyridin-3yl)benzene-1,3-diol (3) | 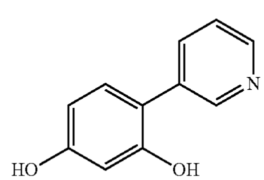 [SMILES: Oc1ccc(-c2cccnc2)c(O)c1] | IC$_{50}$: = 0.5 µM |
| 4-(4'-Hydroxybiphenyl)benzene-1,3-diol (4) | 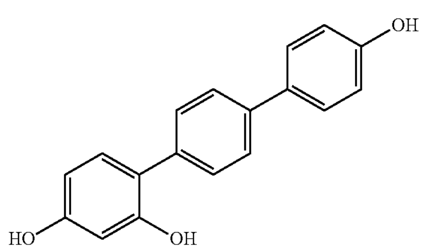 [SMILES: Oc1ccc(-c2ccc(-c3ccc(O)cc3O)cc2)cc1] | IC$_{50}$: = 70.0 µM |

Scheme 2

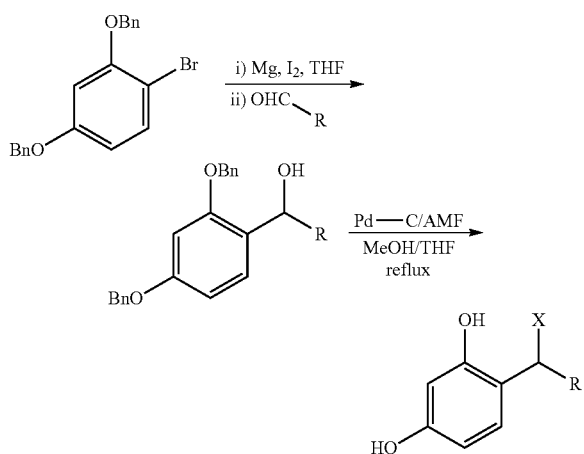

Representative Procedure for Scheme 2: Synthesis of 4-(Furan-2-ylmethyl)benzene-1,3-diol (5)

Benzyl protected 4-bromoresorcinol (2.80 g, 15 mmol) was treated with magnesium turnings (480 mg, 20 mmol) and iodine (a pinch) in THF to provide the corresponding Grignard reagent, which was then added to a stirred solution of 2-furaldehyde (3.97 g, 10 mmol) in THF at 0° C. The reaction mixture was allowed to warm up to room temperature and stirred at room temperature for 3 h. The mixture was then quenched with ammonium chloride, extracted with ethyl acetate, washed with brine and dried over anhydrous $Na_2SO_4$, filtered, concentrated in a rotary evaporator and purified by column chromatography to provide (3.0 g, 80%) of the coupled product.

The coupled product (2.5 g, 6.5 mmol) was then treated with a catalytic amount of 10% Pd on activated carbon (250 mg) and an excess amount of ammonium formate (3.33 g, 52 mmol) in THF/MeOH (18 mL) at reflux to remove the benzyl protecting groups. Partial dehydroxylation of benzyl hydroxy group also took place during the debenzylation reaction. Upon completion, the reaction mixture was filtered through Celite to remove the catalyst and concentrated to provide the crude product, which was then purified by column chromatography to yield (740 mg, 60%) of compound 5 as an off-white solid, as well as, the hydroxylated compound (X=OH) (270 mg, 20%). $^1$H-NMR (MeOD, 500 MHz): δ 7.306 (dd, 1H, J=1.0 & 2.0 Hz), 6.8565 (d, 1H, J=8.5 Hz), 6.8085 (d, 1H, J=8.5 Hz), 6.3155 (d, 1H, J=2.5 Hz), 6.2965 (d, 1H, J=2.5 Hz), 6.255-6.223 (m, 2H). $^{13}$C-NMR (MeOD, 125 MHz): δ 156.604 (C), 156.504 (C), 156.064 (C), 155.556 (C), 155.290 (C), 140.575 (CH), 131.443 (CH), 130.325 (CH), 116.098 (C), 116.973 (C), 109.761 (CH), 106.303 (CH), 106.111 (CH), 105.156 (CH), 102.513 (CH), 102.061 (CH), 79.946 (CH), 67.489 ($CH_2$), 35.257 (CH), 29.875 ($CH_2$), 27.102 ($CH_2$), 25.218 ($CH_2$).

Representative compounds 6-11 of Formula II (see Table 2) were synthesized according to the same general reaction scheme using the appropriate staring materials. Overall yields varied from 50-60%.

4-(Furan-3-ylmethyl)benzene-1,3-diol (6)

$^1$H-NMR (MeOD, 500 MHz): δ 8.39 (d, 1H, J=2 Hz), 8.28 (dd, 1H, J=5 & 1.5 Hz), 6.63-6.69 (m, 1H), 7.25-7.28 (m, 1H), 6.87 (d, 1H, J=8.5 Hz), 6.31 (d, 1H, J=2.5 Hz), 6.24 (dd, 1H, J=8 & 2.5 Hz), 3.25 (s, 2H). $^{13}$C-NMR (MeOD, 125 MHz): δ 156.897 (C), 155.797 (C), 148.727 (CH), 145.584 (CH), 138.672 (C), 137.021 (CH), 130.536 (CH), 123.476 (CH), 117.446 (C), 106.221 (CH), 102.283 (CH), 32.196 ($CH_2$).

4-(Pyridin-ylmethyl)benzene-1,3-diol (7)

$^1$H-NMR (MeOD, 500 MHz): δ 8.39 (d, 1H, J=2 Hz), 8.28 (dd, 1H, J=5 & 1.5 Hz), 6.63-6.69 (m, 1H), 7.25-7.28 (m, 1H), 6.87 (d, 1H, J=8.5 Hz), 6.31 (d, 1H, J=2.5 Hz), 6.24 (dd, 1H, J=8 & 2.5 Hz), 3.25 (s, 2H). $^{13}$C-NMR (MeOD, 125 MHz): δ 156.897 (C), 155.797 (C), 148.727 (CH), 145.584 (CH), 138.672 (C), 137.021 (CH), 130.536 (CH), 123.476 (CH), 117.446 (C), 106.221 (CH), 102.283 (CH), 32.196 ($CH_2$).

Hydroxylated product (20%) was also obtained and was successfully separated by column chromatography (See compound 11 below).

4-((2-Methoxypyridin-3-yl)methyl)benzene-1,3-diol (8)

$^1$H-NMR (MeOD, 500 MHz): δ 7.9015 (dd, 1H, J=1.5 & 5.0 Hz), 7.277 (dt, 1H, J=1.0 & 7.0 Hz), 6.778-6.823 (m, 2H), 6.313 (dd, 1H, J=2.5 & 6.5 Hz), 6.239 (dt, 1H, J=2.0 & 8.5 Hz), 3.935 (s, 3H), 3.749 (s, 2H). $^{13}$C-NMR (MeOD, 125 MHz): δ 161.927 (C), 157.766 (C), 156.578 (C). 155.941 (C), 143.115 (CH), 137.880 (CH), 130.828 (CH), 124.794 (C), 116.498 (CH), 106.133 (CH), 102.098 (CH), 52.482 ($CH_3$), 28.505 ($CH_2$).

4-(2,4,6-trimethoxybenzyl)benzene-1,3-diol (9)

$^1$H-NMR (MeOD, 500 MHz): δ 6.587 (d, 1H, J=8.5 Hz), 6.242 (s, 1H), 6.239 (s, 2H), 6.106 (dd, 1H, J=2.5 & 8.0 Hz), 3.798 (s, 3H), 3.775 (s, 6H), 3.703 (s, 2H). $^{13}$C-NMR ($CDCl_3$, 125 Hz): δ 160.150 (C), 158.100 (2C), 155.986 (C), 155.509 (C), 132.723 (CH), 119.535 (C), 109.882 (C), 107.232 (CH), 103.475 (CH), 91.531 (2CH), 56.258 (2$CH_3$), 55.802 ($CH_3$), 23.157 ($CH_2$).

4-(Benzo[d][1,3]dioxol-5-ylmethyl)benzene-1,3-diol (10)

$^1$H-NMR (MeOD, 500 MHz): δ 6.775 (d, 1H, J=8.5 Hz), 6.62-6.68 (m, 3H), 6.295 (d, 1H, J=2.0 Hz), 6.202-6.223 (m, 1H), 5.842 (s, 2H), 3.733 (s, 2H). $^{13}$C-NMR (MeOD, 125 MHz): δ 155.840 (C), 155.124 (C), 148.362 (C), 146.548 (C), 134.234 (C), 131.868 (CH), 121.597 (CH), 119.754 (C), 109.431 (CH), 108.687 (CH), 108.154 (CH), 103.761 (CH), 101.299 ($CH_2$), 35.949 ($CH_2$).

4-(hydroxyl(pyridine-3-yl)methyl)benzene-1,3-diol (11)

$^1$H-NMR (MeOD, 300 MHz): δ 8.528 (d, 1H, J=2.1 Hz), 8.355 (dd, 1H, J=3.6 & 4.8 Hz), 7.820 (td, J=1.5 & 7.5 Hz), 7.353 (t, 1H, J=5.4 Hz), 7.086 (d, 1H, J=7.8 Hz), 6.315-6.267 (m, 2H), 6.067 (s, 1H); Minor partial: 8.497 (d, 1H, J=2.1 Hz), 7.018 (d, 1H, J=9.3 Hz), 5.661 (s, 1H). $^{13}$C-NMR (MeOD, 125 MHz): δ 157.659 (C), 155.283 (C), 147.120 (CH), 146.694 (CH), 141.308 (C), 135.144 (CH), 127.604 (CH), 123.495 (CH), 120.885 (C), 106.466 (CH), 102.231 (CH), 68.285 (CH).

TABLE 2

Compounds Representative of Formula II

| Compound | Structure | Mushroom Tyrosinase Assay |
|---|---|---|
| 4-(Furan-2-ylmethyl)benzene-1,3-diol (5) | 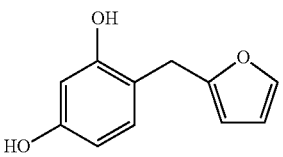 [SMILES: Oc1ccc(Cc2ccco2)c(O)c1] | $IC_{50}$: = 1.8 μM |
| 4-(Furan-3-ylmethyl)benzene-1,3-diol (6) | 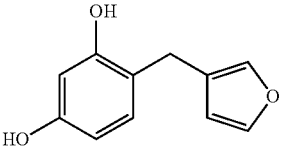 [SMILES: Oc1ccc(Cc2ccoc2)c(O)c1] | $IC_{50}$: = 3.0 μM |
| 4-(Pyridin-ylmethyl)benzene-1,3-diol (7) | 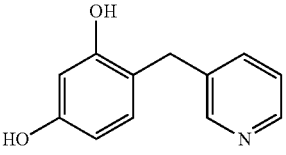 | $IC_{50}$: = 2.0 μM |
| 4-((2-Methoxypyridin-3-yl)methyl)benzene-1,3-diol (8) | 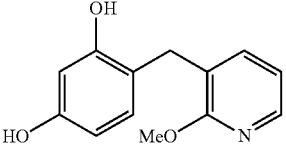 | $IC_{50}$: = 50.0 μM |
| 4-(2,4,6-trimethoxybenzyl)benzene-1,3-diol (9) | 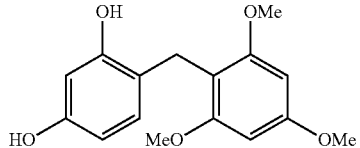 [SMILES: COc1cc(OC)c(Cc2ccc(O)cc2O)c(OC)c1] | $IC_{50}$: = 30.0 μM |
| 4-(Benzo[d][1,3]dioxol-5-ylmethyl)benzene-1,3-diol (10) | 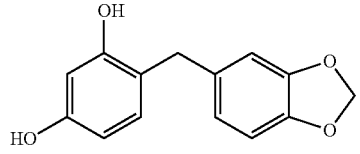 [SMILES: Oc1ccc(Cc2ccc3c(c2)OCO3)c(O)c1] | $IC_{50}$: = 0.85 μM |
| 4-(hydroxyl(pyridine-3-yl)methyl)benzene-1,3-diol (11) | 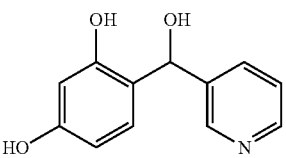 [SMILES: Oc1ccc(C(O)c2cccnc2)c(O)c1] | $IC_{50}$: = 4.9 μM |

Example 3. General and Specific Methods for the Synthesis of Compounds of Formula III

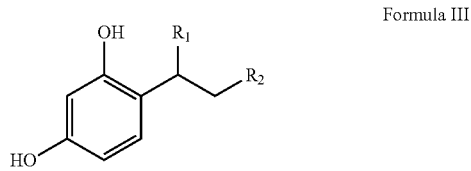

Formula III

Compounds of Formula III were prepared as illustrated in Scheme 3, below. Briefly, with reference to Scheme 3, the 1,2-diphenylethene compounds of Formula III were prepared by Wittig reaction between the corresponding Wittig salt and aldehyde followed by hydrogenation with Pd on activated carbon and ammonium formate (AMF).

Scheme 3

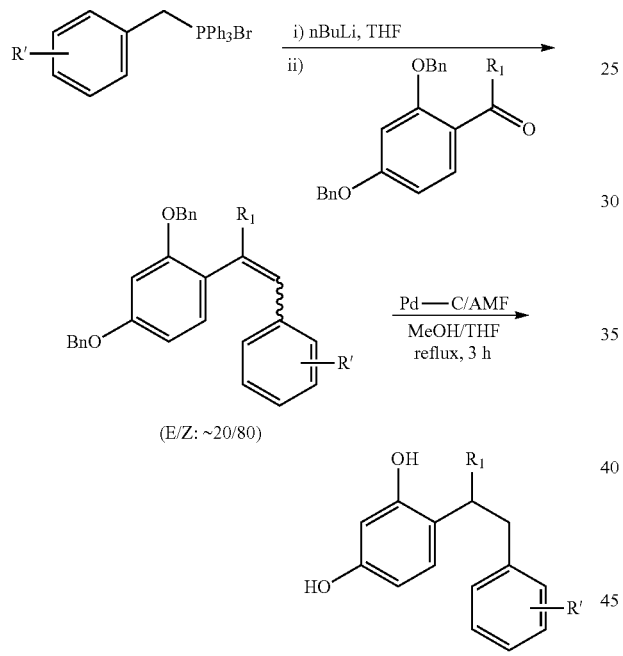

Representative Procedure for Scheme 3:
4-Phenethylbenzene-1,3-diol (12)

To a solution of the phosphonium salt of benzyl bromide (5.2 g, 12 mmol) in THF (25 mL), nBu-Li in hexane (6.9 mL, 11 mmol) was added at 0° C. The reaction mixture was allowed to stir at room temperature for 1 h, during which time the mixture developed a red color indicating the formation of ylide. A solution of 2,4-bis(benzoloxy)benzaldehyde (3.2 g, 10 mmol) in THF (10 mL) was added to the ylide solution at −80° C. and allowed to stir overnight without removing the low temperature bath. During that period the red color was disappeared and a whitish suspension was formed which was diluted with hexane and filtered. The filtrate was concentrated and the residue was passed through a short bed of silica gel eluting with ethyl acetate-hexane (5:95) to yield the coupled product (3.6 g, 92%) in a ratio of (E/Z: 20/80) as a pale yellow oil.

The coupled product (3 g, 7.7 mmol) was then dissolved in 24 mL THF/MeOH (1:2) followed by treatment with 10% Pd on activated carbon (300 mg) and ammonium formate (3.92 g, 62 mmol) at reflux for 4 h. After cooling, the reaction mixture was filtered through celite to remove the catalyst. The crude product was purified by column chromatography eluting with hexane and ethyl acetate (75:25) to yield compound 12 (1.5 g, 95%) as off-white solid. $^1$H-NMR (MeOD, 500 MHz): δ 7.19-7.09 (m, 5H), 7.77 (d, 1H, J=8 Hz), 6.35 (t, 1H, J=2.5 Hz), 6.22 (s, 1H), 2.80 (d, 2H, J=6 Hz), 2.78 (d, 2H, J=4 Hz). $^{13}$C-NMR (MeOD, 125 MHz): δ 155.911 (C), 155.604 (C), 142.535 (C), 130.302 (CH), 128.177 (CH), 128.170 (CH), 127.815 (CH), 127.800 (CH), 125.238 (CH), 119.561 (C), 106.029 (CH), 102.150 (CH), 36.274 (CH$_2$), 31.803 (CH$_2$).

Representative compounds 13-27 of Formula III (see Table 3) were synthesized according to the same general reaction scheme using the appropriate staring materials. Overall yields varied from 35-55%. In some cases, the reductive high pressure hydrogenation reaction was successfully performed using Parr apparatus instead of CTH methods to obtain the final compounds.

4-(4-hydroxyphenethylbenzene)-1,3-diol (13)

$^1$H-NMR (MeOD, 500 MHz): δ 6.985 (dd, 2H, J=3 & 5 Hz), 6.764 (d, 1H, J=8 Hz), 6.716-6.617 (m, 2H), 6.326 (d, 1H, J=2.5 Hz), 6.215 (dd, 1H, J=2.5 & 8.5 Hz), 2.719 (s, 2H), 2.675 (d, 2H, J=8.5 Hz). $^{13}$C-NMR (MeOD, 125 MHz): δ 155.756 (C), 155.500 (C), 154.560 (C), 133.707 (C), 130.354 (CH), 129.125 (2CH), 119.742 (C), 114.586 (2CH), 106.048CH), 102.127 (CH), 35.393 (CH$_2$), 31.988 (CH$_2$).

4-(4-methoxyphenethyl)benzene-1,3-diol (14)

$^1$H-NMR (MeOD, 500 MHz): δ 7.052 (d, 2H, J=8.5 Hz), 6.748-6.772 (m, 3H), 6.343 (d, 1H, J=2.5 Hz), 6.222 (dd, 1H, J=2.5 & 8.0 Hz), 3.683 (s, 3H), 2.745 (t, 4H, J=6.0 Hz). $^{13}$C-NMR (MeOD, 125 MHz): δ 157.700 (C), 155.893 (C), 155.601 (C), 134.660 (C), 130.317 (CH), 129.073 (2CH), 119.608 (C), 113.255 (2CH), 106.007 (CH), 102.139 (CH), 54.303 (CH$_3$), 35.350 (CH$_2$), 31.944 (CH$_2$).

4-(2-(benzo[d][1,3]dioxol-5-ylethyl)benzene-1,3-diol (15)

$^1$H-NMR (MeOD, 500 MHz): δ 6.75 (d, 1H, J=8 Hz), 6.67 (d, 1H, J=8 Hz), 6.66 (d, 1H, J=1.5 Hz), 6.61 (dd, 1H, J=8 & 1.5 Hz), 6.27 (d, 1H, J=2.5 Hz), 6.17 (dd, 1H, J=8 & 2.5 Hz), 5.87 (s, 2H), 2.71-2.72 (m, 4H). $^{13}$C-NMR (MeOD, 125 MHz): δ 156.01 (C), 155.01 (C), 147.41 (C), 145.47 (C), 136.52 (C), 130.14 (CH), 120.87 (CH), 119.23 (C), 108.48 (CH), 107.39 (CH), 105.82 (CH), 102.03 (CH), 100.45 (CH$_2$), 35.95 (CH$_2$), 32.03 (CH$_2$).

4,4'-(ethane-1,2diyl)dibenzene-1,3-diol (16)

$^1$H-NMR (MeOD, 500 MHz): δ 6.81 (d, 2H, J=2 Hz), 6.29 (s, 2H), 6.20 (dd, 2H, J=2 & 2 Hz), 2.68 (s, 4H). $^{13}$C-NMR (MeOD, 125 MHz): δ 155.83 (2C), 155.47 (2C), 130.04 (2CH), 145.47 (C), 120.01 (2C), 105.95 (2CH), 102.05 (2CH), 30.04 (2CH$_2$).

4-(2,4-dimethoxyphenethyl)benzene-1,3-diol (17)

$^1$H-NMR (MeOD, 500 MHz): δ 6.93 (d, 1H, J=8 Hz), 6.73 (d, 1H, J=8 Hz), 6.46 (d, 1H, J=2 Hz), 6.37 (dd, 1H, J=8 &

2 Hz), 6.28 (d, 1H, J=2 Hz), 6.17 (dd, 1H, J=8 & 2 Hz), 3.77 (s, 3H), 3.74 (s, 3H), 2.67-2.73 (m, 4H). $^{13}$C-NMR (MeOD, 125 MHz): δ 159.177 (C), 158.307 (C), 155.801 (C), 155.564 (C), 155.564 (C), 130.047 (CH), 129.758 (CH), 122.988 (C), 119.900 (C), 105.796 (CH), 103.771 (CH), 101.991 (CH), 97.867 (CH), 54.392 (CH$_3$), 54.289 (CH$_3$), 29.901 (CH$_2$), 29.834 (CH$_2$).

4-(3,5-dimethoxyphenethyl)benzene-1,3-diol (18)

$^1$H-NMR (MeOD, 500 MHz): δ 6.77 (d, 1H, J=10 Hz), 6.34 (d, 2H, J=5 Hz), 6.32 (d, 1H, J=5 Hz), 6.25 (t, 1H, J=5 Hz), 6.20 (dd, 1H, J=10 & 5 Hz), 3.68 (s, 6H), 2.75 (s, 4H). $^{13}$C-NMR (MeOD, 125 MHz): δ 160.67 (C, 2C), 155.98 (C), 155.60 (C), 144.91 (C), 130.32 (CH), 119.38 (C), 106.20 (CH, 2C), 105.97 (CH), 102.08 (CH), 97.50 (CH), 54.25 (2 CH$_3$), 36.48 (CH$_2$), 31.47 (CH$_2$).

4-(2,4-dimethoxy-3-methylphenethyl)benzene-1,3-diol (19)

$^1$H-NMR (MeOD, 500 MHz): δ 6.972 (d, 1H, J=8.5 Hz), 6.624 (d, 1H, J=9.0 Hz), 6.285 (dd, 1H, J=1 & 2.5 Hz), 6.184 (ddd, 1H, J=1.5, 2.5 & 8 Hz), 3.783 (s, 3H), 3.694 (s, 3H), 2.723-2.762 (m, 4H), 2.114 (s, 3H). $^{13}$C-NMR (MeOD, 125 MHz): δ 157.034 (C), 156.915 (C), 155.953 (C), 155.664 (C), 130.066 (CH), 127.197 (C), 126.967 (CH), 119.834 (C), 118.705 (C), 105.855 (CH), 105.841 (CH), 102.046 (CH), 59.749 (CH$_3$), 54.637 (CH$_3$), 31.008 (CH$_2$), 29.916 (CH$_2$), 7.941 (CH$_3$).

4-(2,4,6-trimethoxyphenethyl)benzene-1,3-diol (20)

$^1$H-NMR (MeOD, 500 MHz): δ 6.698. (dd, 1H, J=1.5 & 8 Hz), 6.262 (t, 1H, J=2.5 Hz), 6.135-6.157 (m, 3H), 3.775 (s, 3H), 3.730 (s, 3H), 3.723 (s, 3H), 2.750 (t, 2H, J=8.0 Hz), 2.563 (t, 2H, J=8.0 Hz). $^{13}$C-NMR (MeOD, 125 MHz): δ 159.369 (C), 158.799 (2C), 155.638 (C), 155.556 (C), 129.840 (CH), 120.359 (C), 111.082 (C), 105.696 (CH), 101.906 (CH), 90.367 (2CH), 54.744 (2CH$_3$), 54.281 (CH$_3$), 28.790 (CH$_2$), 22.653 (CH$_2$).

4-(1-phenylpropan-2-yl)benzene-1,3-diol (21)

$^1$H-NMR (MeOD, 500 Hz): δ 6.928 (d, 2H, J=8.5 Hz), 6.8541 (d, 1H, J=8.0 Hz), 6.631 (d, 2H, J=8.0 Hz), 6.259 (d, 1H, J=2.0 Hz), 6.219 (dd, 1H, J=2.5 & 8.0 Hz), 3.231 (q, 1H, J=6.5 Hz), 2.854 (dd, 1H, J=5.5 & 13.0 Hz), 2.519 (dd, 1H, J=9.0 & 13.5 Hz), 1.087 (d, 3H, J=7.0 Hz). $^{13}$C-NMR (MeOD, 500 Hz): δ 155.482 (C), 155.093 (C), 153.428 (C), 154.716 (C), 132.452 (CH), 129.673 (2CH), 124.583 (C), 114.242 (2CH), 105.870 (CH), 102.016 (CH), 42.284 (CH$_2$), 33.835 (CH), 18.575 (CH$_3$).

4-(2-(furan-3-yl)ethyl)benzene-1,3-diol (22)

$^1$H-NMR (CDCl$_3$, 300 MHz): δ 7.348 (s, 2H), 7.187 (s, 1H), 6.342 (d, 1H, J=8.1 Hz), 6.282 (d, 2H, J=10.2 Hz), 2.795-2.663 (m, 4H). $^{13}$C-NMR (CDCl$_3$, 75 MHz): δ 154.903 (C), 154.594 (C), 143.043 (CH), 139.307 (CH), 131.236 (CH), 124.802 (C), 120.509 (C), 111.259 (CH), 107.970 (CH), 103.249 (CH), 30.310 (CH$_2$), 25.544 (CH$_2$).

4-(2-(tetrahydrofuran-3-yl)ethyl)benzene-1,3-diol (23)

$^1$H-NMR (CDCl$_3$, 300 MHz): δ 6.933 (d, 1H, J=8.4 Hz), 6.359-6.283 (m, 2H), 3.951-3.709 (m, 3H), 3.388 (t, 1H, J=7.5 Hz), 2.602-2.492 (m, 2H), 2.262-2.163 (m, 2H), 1.707-1.585 (m, 3H). $^{13}$C-NMR (CDCl$_3$, 75 MHz): δ 155.056, 154.544, 132.595, 120.639, 110.008, 107.810, 103.074, 68.188, 64.108, 33.905, 32.718, 28.432.

4-(2-(furan-2-yl)ethyl)benzene-1,3-diol (24)

$^1$H-NMR (MeOD, 500 MHz): δ 7.31 (d, 1H, J=2 Hz), 6.78 (d, 1H, J=8 Hz), 6.28 (d, 1H, J=2 Hz), 6.24 (dd, 1H, J=3 & 2 Hz), 6.18 (dd, 1H, J=8 & 2.5 Hz), 5.95 (dd, 1H, J=3 Hz), 2.78-2.82 (m, 4H). $^{13}$C-NMR (MeOD, 125 MHz): δ 156.145 (C), 156.104 (C), 155.675 (C), 140.334 (CH), 129.995 (CH), 118.790 (C), 109.576 (CH), 105.867 (CH), 104.315 (CH), 102.020 (CH), 28.209 (CH$_2$), 28.150 (CH$_2$).

4-(2-(tetrahydrofuran-2-yl)ethyl)benzene-1,3-diol (25)

$^1$H-NMR (MeOD, 500 MHz): δ 6.83 (d, 1H, J=8 Hz), 6.26 (d, 1H, J=2.5 Hz), 6.21 (dd, 1H, J=8 & 2.5 Hz), 3.79-3.85 (m, 2H), 3.70-3.73 (m, 1H), 2.57-2.60 (m, 1H), 2.51-2.56 (m, 1H), 1.98-2.01 (m, 1H), 1.86-1.90 (m, 2H), 1.77-1.80 (m, 1H), 1.70-1.71 (m, 1H), 1.48-1.54 (m, 1H). $^{13}$C-NMR (MeOD, 125 MHz): δ 156.01 (C), 155.619 (C), 155.675 (C), 129.958 (CH), 119.326 (C), 105.855 (CH), 102.130 (CH), 79.187 (CH), 67.104 (CH$_2$), 35.728 (CH$_2$), 30.771 (CH$_2$), 25.951 (CH$_2$), 25.218 (CH$_2$).

4-(2-(5-ethylofuran-2-yl)ethyl)benzene-1,3-diol (26)

$^1$H-NMR (MeOD, 500 MHz): δ 6.786 (d, 1H, J=8.0 Hz), 6.278 (d, 1H, J=2.5 Hz), 6.1845 (dd, 1H, J=2.5 & 8.0 Hz), 5.189 (s, 2H), 2.766 (s, 4H), 2.578 (q, 2H, J=7.5 Hz), 1.194 (td, 3H, J=7.5 & 1.0 Hz). $^{13}$C-NMR (MeOD, 125 MHz): δ 156.090 (C), 155.649 (C), 155.401 (C), 154.142 (C), 129.999 (CH), 118.938 (C), 105.852 (CH), 104.734 (CH), 103.779 (CH), 102.006 (CH), 28.309 (CH$_2$), 28.268 (CH$_2$), 20.828 (CH$_2$), 11.443 (CH$_3$).

4-(2-(pyridin-3yl)ethyl)benzene-1,3-diol (27)

$^1$H-NMR (MeOD, 300 MHz): δ 8.293 (dd, 1H, J=4.8 & 1.5 Hz), 8.250 (d, 1H, J=1.8 Hz), 7.605 (dt, 1H, J=8.1 & 1.5 Hz), 7.291 (ddd, 1H, J=7.5, 4.5 & 0.6 Hz), 6.673 (d, 1H, J=8.4 Hz), 6.270 (d, 1H, J=2.4 Hz), 6.139 (dd, 1H, J=8.4 & 2.1 Hz), 2.880 (td, 2H, J=6.6 & 1.8 Hz), 2.778 (td, 2H, J=6.6 & 1.2 Hz). $^{13}$C-NMR (MeOD, 125 MHz): δ 156.06 (C), 156.04 (CH), 149.00 (CH), 146.00 (CH), 138.90 (C), 137.34 (CH), 130.57 (CH), 123.72 (CH), 118.31 (C), 106.03 (CH), 102.25 (CH), 33.14 (CH$_2$), 31.48 (CH$_2$).

TABLE 3

Compounds Representative of Formula III

| Compound | Structure | Mushroom Tyrosinase Assay |
|---|---|---|
| 4-Phenethylbenzene-1,3-diol (12) | 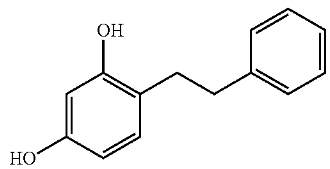 [SMILES: Oc1ccc(CCc2ccccc2)c(O)c1] | IC$_{50}$: = 2.8 μM |
| 4-(4-hydroxyphenethylbenzene)-1,3-diol (13) | 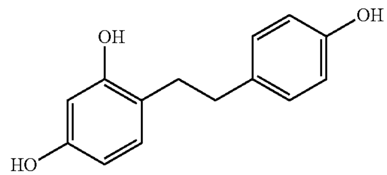 [SMILES: Oc1ccc(CCc2ccc(O)cc2O)cc1] | IC$_{50}$: = 2.9 μM |
| 4-(4-methoxyphenethyl)benzene-1,3-diol (14) | 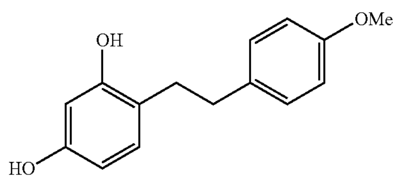 [SMILES: COc1ccc(CCc2ccc(O)cc2O)cc1] | IC$_{50}$: = 1.2 μM |
| 4-(2-(benzo[d][1,3]dioxol-5-ylethyl)benzene-1,3-diol (15) | 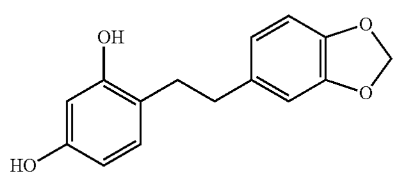 [SMILES: Oc1ccc(CCc2ccc3c(c2)OCO3)c(O)c1] | IC$_{50}$: = 0.25 μM |
| 4,4'-(ethane-1,2diyl)dibenzene-1,3-diol (16) | 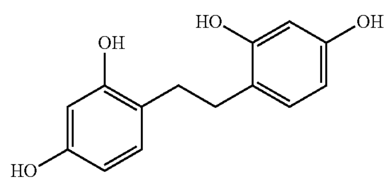 [SMILES: Oc1ccc(CCc2ccc(O)cc2O)c(O)c1] | IC$_{50}$: = 0.35 μM |
| 4-(2,4-dimethoxyphenethyl)benzene-1,3-diol (17) | 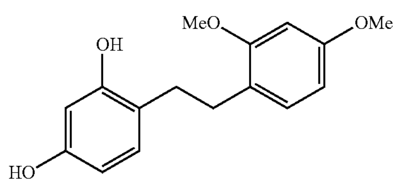 [SMILES: COc1ccc(CCc2ccc(O)cc2O)c(OC)c1] | IC$_{50}$: = 3.0 μM |
| 4-(3,5-dimethoxyphenethyl)benzene-1,3-diol (18) | 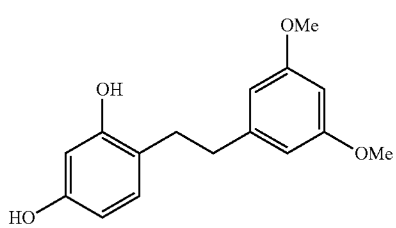 [SMILES: COc1cc(CCc2ccc(O)cc2O)cc(OC)c1] | IC$_{50}$: = 2.8 μM |
| 4-(2,4-dimethoxy-3-methylphenethyl)benzene-1,3-diol (19) | 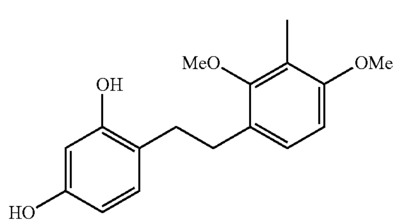 [SMILES: COc1ccc(CCc2ccc(O)cc2O)c(OC)c1C] | IC$_{50}$: = 0.80 μM |

TABLE 3-continued

Compounds Representative of Formula III

| Compound | Structure | Mushroom Tyrosinase Assay |
| --- | --- | --- |
| 4-(2,4,6-trimethoxyphenethyl)benzene-1,3-diol (20) | 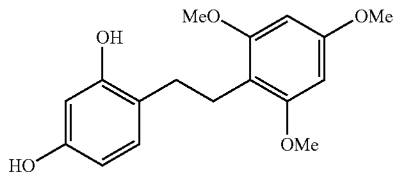 [SMILES: COc1cc(OC)c(CCc2ccc(O)cc2O)c(OC)c1] | IC$_{50}$: = 40.0 µM |
| 4-(1-phenylpropan-2-yl)benzene-1,3-diol (21) | 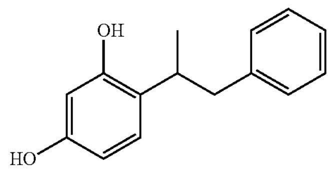 [SMILES: CC(Cc1ccccc1)c1ccc(O)cc1O] | IC$_{50}$: = 8.4 µM |
| 4-(2-(furan-3-yl)ethyl)benzene-1,3-diol (22) | 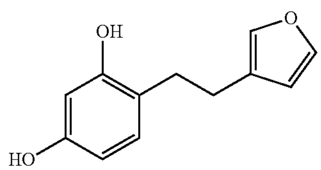 [SMILES: Oc1ccc(CCc2ccoc2)c(O)c1] | IC$_{50}$: = 1.0 µM |
| 4-(2-(tetrahydrofuran-3-yl)ethyl)benzene-1,3-diol (23) | 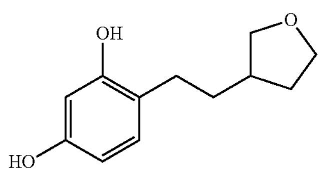 [SMILES: Oc1ccc(CCC2CCOC2)c(O)c1] | IC$_{50}$: = 5.8 µM |
| 4-(2-(furan-2-yl)ethyl)benzene-1,3-diol (24) | 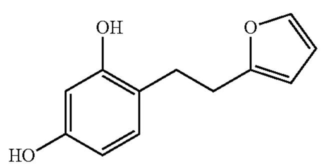 [SMILES: Oc1ccc(CCc2ccco2)c(O)c1] | IC$_{50}$: = 0.2 µM |
| 4-(2-(tetrahydrofuran-2-yl)ethyl)benzene-1,3-diol (25) | 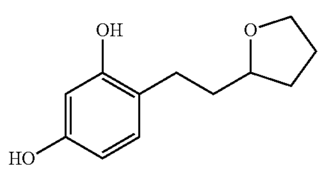 [SMILES: Oc1ccc(CCC2CCCO2)c(O)c1] | IC$_{50}$: = 4.5 µM |
| 4-(2-(5-ethylofuran-2-yl)ethyl)benzene-1,3-diol (26) | 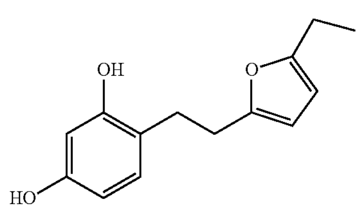 [SMILES: CCc1ccc(CCc2ccc(O)cc2O)o1] | IC$_{50}$: = 0.86 µM |
| 4-(2-(pyridin-3yl)ethyl)benzene-1,3-diol (27) | 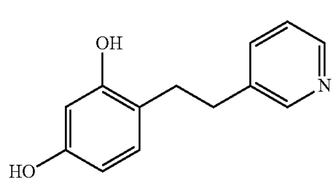 [SMILES: Oc1ccc(CCc2cccnc2)c(O)c1] | IC$_{50}$: = 1.8 µM |

Example 4. General and Specific Methods for the Synthesis of Compounds of Formula IV

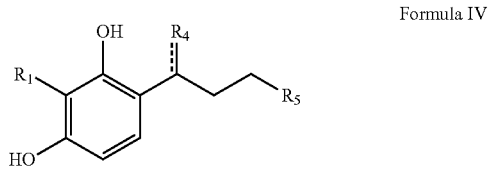

Formula IV

Compounds of Formula IV were prepared as described in Scheme 4. Briefly, the 1,3-diphenylpropanes illustrative of Formula IV were prepared by base catalyzed Aldol condensation to provide the respective chalcones, which were then reduced by catalytic transfer of hydrogen (CTH) using ammonium formate (AMF) and a Pd—C catalyst.

Scheme 4

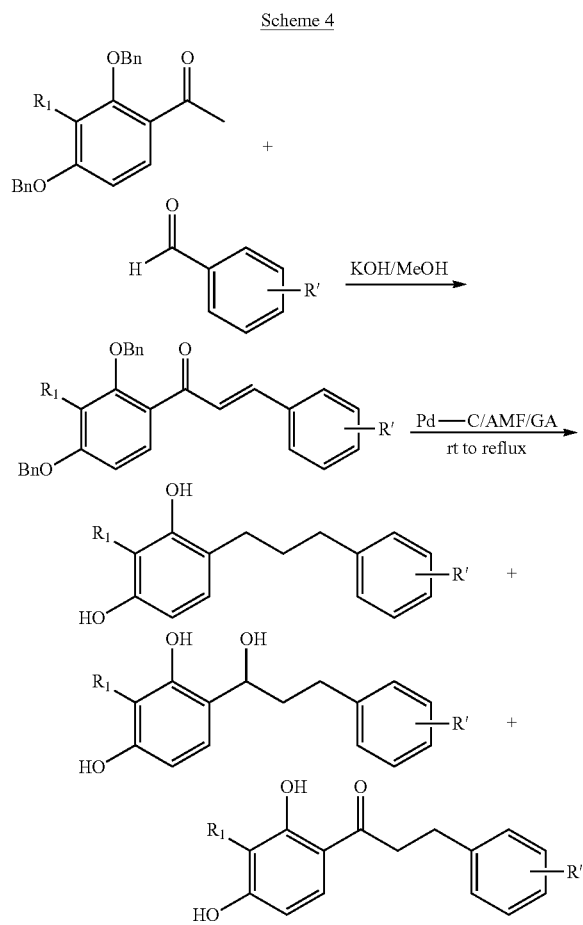

Representative Procedure for Scheme 4: Synthesis of Compounds 28, 29 and 30

General Method for Aldol Condensation Reaction

To a solution containing 2,4-dibenzyloxyacetophenone (7.67 g, 23.1 mmol) and 3,5-dimethoxybenzaldehyde (3.80 g, 23 mmol) in 100 mL anhydrous MeOH was added KOH (1.4 g, 25 mmol) and the mixture was stirred for 5 h at room temperature. A yellow solid was precipitated out which was filtered and washed with water. The crude product was finally crystallized from MeOH to afford a yellow crystalline solid (9.97 g; 87%).

General Method for CTH Reduction

The condensation product, α,β-unsaturated ketone (3 g, 7.5 mmol) was dissolved in 24 mL glacial acetic acid followed by the addition of 10% Pd on activated carbon (300 mg) and ammonium formate (3.92 g, 62 mmol) and the reaction mixture was refluxed for 4 h. After cooling down the reaction mixture was filtered through Celite to remove the catalyst. The crude product was concentrated at rotary evaporator and purified by column chromatography eluting with hexane and ethyl acetate (75:25) to yielded compound 28 (1.1 g, 50%) as off-white solid & compound 29 (0.57 g, 25%) as thick yellow liquid.

General Method for Demethylation

To a stirred solution of 28 (1.4 g, 4.9 mmol) in dry $CH_2Cl_2$ (20 mL) under argon at −80° C., $BBr_3$ (2.67 g 10.7 mmol) was added and the mixture was slowly warmed to 0° C. The reaction was quenched by adding ice-cooled water and methanol was added. The solvent was then removed in a rotary evaporator and the crude product was purified by column chromatography eluting with ethyl acetate/hexanes (25:75) to provide compound 30 (1.14 g, 90%) as a solid.

4-(3-(3,5-dimethoxyphenyl)propyl)benzene-1,3-diol (28)

$^1$H-NMR (MeOD, 500 MHz): δ 6.828 (d, 1H, J=8.5 Hz), 6.344 (d, 2H, J=2.5 Hz), 6.288 (d, 1H, J=2.5 Hz), 2.265 (t, 1H, J=2.0 Hz), 6.226 (dd, 1H, J=2.5 Hz & 8.0 Hz), 3.723 (s, 6H), 2.503-2.558 (m, 4H), 1.800-1.826 (m, 2H). $^{13}$C-NMR (MeOD, 125 MHz): δ 160.772 (2C), 155.860 (C), 155.597 (C), 145.065 (C), 130.080 (CH), 119.774 (C), 106.055 (2CH), 105.937 (CH), 102.094 (CH), 97.326 (CH), 54.226 (2CH$_3$), 35.587 (CH$_2$), 31.563 (CH$_2$), 28.924 (CH$_2$).

4-(3-(3,5-dimethoxyphenyl)-1-hydroxypropyl)benzene-1,3-diol (29)

$^1$H-NMR (MeOD, 500 MHz): δ 6.977 (d, 1H, J=8.0 Hz), 6.316-6.337 (m, 3H), 6.309 (t, 1H, J=2.5 Hz), 6.259 (t, 1H, J=2.5 Hz), 4.781 (dd, 1H, J=5.5 Hz, J2=7.5 Hz), 3.704 (s, 6H), 2.623 (ddd, 1H, J=13.5 Hz, J2=10.0 Hz, J3=5.5 Hz), 2.5222 (ddd, 1H, J=20.0 Hz, J2=9.5 Hz, J3=6.5 Hz), 2.031-1.908 (m, 2H). $^{13}$C-NMR (MeOD, 125 MHz): δ 160.806 (2C), 157.356 (C), 156.189 (C), 144.503 (C), 128.070 (CH), 118.275 (C), 106.640 (CH), 106.155 (2CH), 102.239 (CH), 97.515 (CH), 78.440 (CH), 54.185 (CH$_3$), 54.059 (CH$_3$), 37.786 (CH$_2$), 32.070 (CH$_2$).

4-(3-(3,5-dihydroxyphenyl)propyl)benzene-1,3-diol (30)

$^1$H-NMR (MeOD, 500 MHz): δ 6.827 (d, 1H, J=8.0 Hz), 6.267 (d, 1H, J=2.0 Hz), 6.211 (dd, 1H, J=2.5 & 8.5 Hz), 6.142 (d, 2H, J=2.0 Hz), 6.074 (t, 1H, J=2.5 Hz), 2.507 (t, 2H, J=8.0 Hz), 2.455 (t, 2H, J=8.0 Hz), 1.76-1.84 (m, 2H). $^{13}$C-NMR (MeOD, 125 MHz): δ 157.848 (2C), 155.849 (C), 155.582 (C), 145.065 (C), 129.995 (CH), 119.793 (C), 106.559 (2CH), 105.859 (CH), 102.054 (CH), 99.514 (CH), 35.420 (CH$_2$), 31.593 (CH$_2$), 28.961 (CH$_2$).

4-(3-(2,4,6-trimethoxyphenyl)propyl)benzene-1,3-diol (31)

Compound 31 was synthesized following a similar procedure as described for compound 28 above using as starting materials 2,4-dibenzyloxyacetophenone and 2,4,6-trimethoxybenzaldehyde. $^1$H-NMR (MeOD, 500 MHz): δ 6.822 (d, 1H, J=8.0 Hz), 6.250 (d, 1H, J=2.5 Hz), 6.197 (dd, 1H, J=2.5 & 8.0 Hz), 6.165 (s, 2H), 3.768 (s, 3H), 3.764 (s, 6H), 2.562 (t, 2H, J=7.5 Hz), 2.461 (t, 2H, J=7.5 Hz), 1.617-1.653 (m, 2H). $^{13}$C-NMR (MeOD, 125 MHz): δ 159.273 (C), 158.729 (2C), 155.556 (C), 155.449 (C), 129.655 (2CH), 120.426 (C), 111.382 (C), 105.789 (CH), 101.968 (CH), 90.285 (CH), 54.655 (2CH$_3$), 54.274 (CH$_3$), 29.716 (CH$_2$), 29.064 (CH$_2$), 22.142 (CH$_2$).

4-(3-(2,4-dihydroxyphenyl)propyl)-2-methylbenzene-1,3-diol (32)

Compound 32 was synthesized following a similar procedure as described for compound 30 using as starting materials 2,4-dibenzyloxyacetophenone and 2,4-dimethoxy-3-methylbenzaldehyde. $^1$H-NMR (MeOD, 500 MHz): δ 6.879 (d, 1H, J=8.5 Hz), 6.747 (d, 1H, J=8.0 Hz), 6.352 (d, 1H, J=1.5 Hz), 6.341 (d, 1H, J=4.0 Hz), 6.285 (dd, 1H, J=8.0 Hz & 2.5 Hz), 2.567 (dd, 4H, J=8.0 & 7.5 Hz), 2.133 (s, 3H), 1.786-1.817 (m, 2H). $^{13}$C-NMR (MeOD, 125 MHz): δ 155.486 (C), 155.316 (C), 153.428 (C), 152.906 (C), 130.295 (CH), 126.523 (CH), 120.933 (C), 120.518 (C), 111.556 (C), 106.788 (CH), 106.377 (CH), 102.283 (CH), 30.767 (CH$_2$), 29.649 (CH$_2$), 29.127 (CH$_2$), 7.833 (CH$_3$).

4-(3-(2,4-dihydroxy-3-methylphenyl)-3-(2,4-dihydroxyphenyl)propane-1-one (33)

Compound 33 was synthesized following a similar procedure as described for compound 28 using as starting materials 2,4-dibenzyloxyacetophenone and 2,4-dimethoxy-3-methylbenzaldehyde. The reduction with Pd-C/ammonium formate was carried out at room temperature instead of refluxing. Demethylation reaction with borontribromide was performed using as similar protocol described as in the procedure for compound 30. $^1$H-NMR (MeOD, 500 MHz): δ 7.628 (d, 1H, J=9.0 Hz), 6.868 (d, 1H, J=8.0 Hz), 6.349 (d, 1H, J=9.0 Hz), 6.283 (d, 1H, J=2.5 Hz), 6.203 (dd, 1H, J=2.5 & 8.0 Hz), 3.127 (t, 2H, J=7.5 Hz), 2.862 (t, 2H, J=7.5 Hz), 2.031 (s, 3H). $^{13}$C-NMR (MeOD, 500 Hz): δ 205.420 (C), 162.894 (C), 162.264 (C), 156.438 (C), 155.782 (C), 130.710 (CH), 129.510 (CH), 118.364 (C), 112.249 (C), 110.820 (C), 106.596 (CH), 105.970 (CH), 102.142 (CH), 47.089 (CH$_2$), 25.810 (CH$_2$), 6.361 (CH$_3$).

Example 5. Synthesis of 4-(5-hydroxyphenyl)benzene-1,3-diol (34)

Compound 34 was synthesized as set forth in Scheme 5

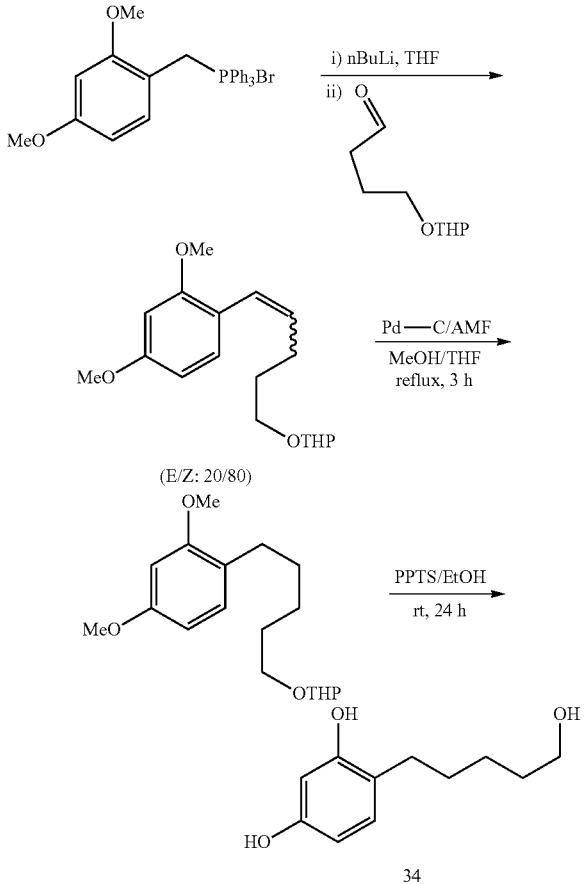

Scheme 5

To a solution of the phosphonium salt of 2,4-bis(benzoloxy)benzyl bromide (7.72, 12 mmol) in THF (25 mL) was added nBu-Li in hexane (6.9 mL, 11 mmol) at 0° C. The reaction mixture was allowed to stir at room temperature for 1 h, during that period the mixture developed a red color indicating the formation of ylide. A solution of 4-(tetrahydropyranyloxy)butanal (1.72 g, 10 mmol) in THF (10 mL) was added to the ylide solution at −80° C. and the mixture was allowed to stir overnight without removing the low temperature bath, during that period the red color disappeared and a whitish suspension was formed which was diluted with hexane and filtered. The filtrate was concentrated and residue was passed through a short bed of silica gel eluting with ethyl acetate-hexane (5:95) to give the coupled product (5.2 g, 92%) in a ratio of (E/Z: 20/80) as pale yellow oil.

The coupled product (3.6 g, 7.7 mmol) was then dissolved in 24 mL THF/MeOH (1:2) followed by treatment with 10% Pd on activated carbon (360 mg) and ammonium formate (3.92 g, 62 mmol) at reflux for 4 h. After cooling down, the reaction mixture was filtered through celite to remove the catalyst. The crude product, after concentration, was purified by column chromatography eluting with hexane and ethyl acetate (80:20) to yield the reduced product (2.15 g, 95%) as a colorless thick liquid.

To a stirred solution of the reduced product (1.2 g, 4 mmol) in ethanol (20 mL) was added pyridinium toluene-4-sulfonate (350 mg, 1.39 mmol) at room temperature and the mixture was stirred for 24 h. Removal of the solvent in vacuum followed by column chromatography of the residue on silica gel eluting with ethyl acetate-hexane (10:90) gave the title compound (34) as off-white solid (690 mg, 88%).

$^1$H-NMR (MeOD, 500 MHz): δ 8.825 (d, 1H, J=7.5 Hz), 6.2705 (d, 1H, J=0.5 Hz), 6.215 (d, 1H, J=7.5 Hz), 3.538 (t, 2H, J=6.5 Hz), 2.491 (t, 2H, J=7.5 Hz), 1.526-1.585 (m, 4H), 1.358-1.40 (m, 2H). $^{13}$C-NMR (MeOD, 125 MHz): δ 155.705 (C), 155.482 (C), 129.984 (CH), 120.108 (C), 105.926 (CH), 102.061 (CH), 61.722 (CH$_2$), 32.189 (CH$_2$), 29.182 (CH$_2$), 29.086 (CH$_2$), 25.322 (CH$_2$), 103.761 (CH).

TABLE 4

Compounds Representative of Formula IV

| Compound | Structure | Mushroom Tyrosinase Assay |
|---|---|---|
| 4-(3-(3,5-dimethoxyphenyl)propyl)benzene-1,3-diol (28) | 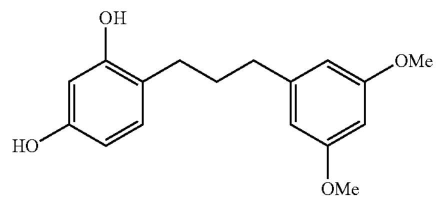 [SMILES: COc1cc(CCCc2ccc(O)cc2O)cc(OC)c1] | IC$_{50}$: = 1.02 μM |
| 4-(3-(3,5-dimethoxyphenyl)-1-hydroxypropyl)benzene-1,3-diol (29) | 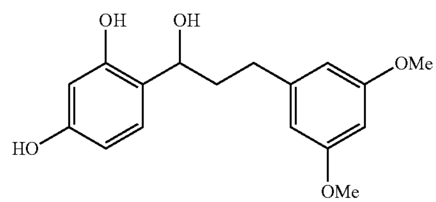 [SMILES: COc1cc(CCC(O)c2ccc(O)cc2O)cc(OC)c1] | IC$_{50}$: = 5.15 μM |
| 4-(3-(3,5-dihydroxyphenyl)propyl)benzene-1,3-diol (30) | 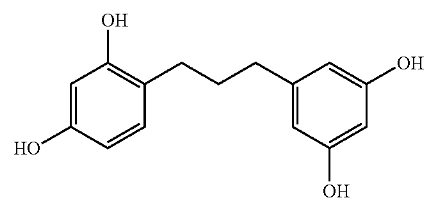 [SMILES: Oc1cc(O)cc(CCCc2ccc(O)cc2O)c1] | IC$_{50}$: = 0.5 μM |
| 4-(3-(2,4,6-trimethoxyphenyl)propyl)benzene-1,3-diol (31) | 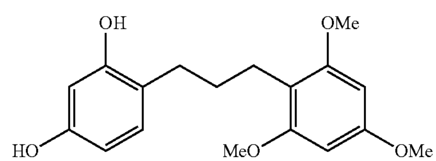 [SMILES: COc1cc(OC)c(CCCc2ccc(O)cc2O)c(OC)c1] | IC$_{50}$: = 0.165 μM |
| 4-(3-(2,4-dihydroxyphenyl)propyl)-2-methylbenzene-1,3-diol (32) | 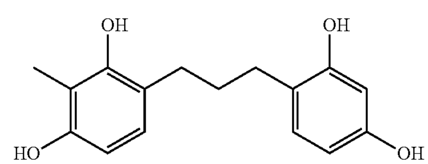 [SMILES: Cc1c(O)ccc(CCCc2ccc(O)cc2O)c1O] | IC$_{50}$: = 2.3 μM |
| 4-(3-(2,4-dihydroxy-3-methylphenyl)-3-(2,4-dihydroxyphenyl)propane-1-one (33) | 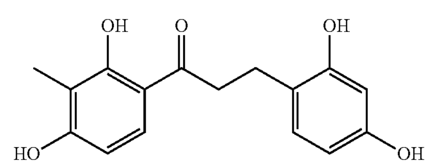 [SMILES: Cc1c(O)ccc(C(=O)CCc2ccc(O)cc2O)c1O] | IC$_{50}$ = 2.54 μM |
| 4-(5-hydroxypentyl)benzene-1,3-diol (34) | 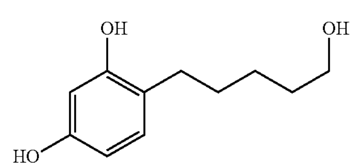 [SMILES: OCCCCCc1ccc(O)cc1O] | IC$_{50}$ = 1.0 μM |

Example 6. Tyrosinase Assay

Reagents

Tyrosinase isolated from the mushroom species *Agaricus bisporus* was purchased from the Sigma-Aldrich Inc. (Cat# T3824-50KU). The enzyme was dissolved in the tyrosinase assay buffer (100 mM sodium phosphate, pH 6.8) to a concentration 10 U/µl, and stored at −70° C. For the experiments the enzyme was freshly diluted in the assay buffer to a concentration of 0.2 U/µl.

All test compounds were initially dissolved in 100% DMSO at a concentration of 400 mM. The compounds were further diluted in 100% DMSO to a concentration of 80 µM. 80 µM stock solutions of the compounds were then diluted ten times in the tyrosinase assay buffer to the concentration of 8 µM. The compounds were then serially diluted at three-fold increments in the assay buffer containing 10% DMSO, keeping the concentration of DMSO constant across all samples. These serially diluted compounds were subsequently used as two-fold concentrated stock solutions in the tyrosinase activity assays.

Tyrosinase substrate, L-DOPA (Sigma-Aldrich Inc, Cat #37830) was dissolved in the tyrosinase assay buffer to a concentration of 4 mM. This solution was then used as the four-fold concentrated stock of substrate in the tyrosinase activity assays.

Assay Conditions

Tyrosinase assays were performed in clear-bottom 96-well plates at room temperature. The final volume of the assays was 200 µl per well. 100 µl of two-fold concentrated test compounds were mixed with 50 µl of 4 mM L-DOPA. The reactions were initiated by adding 50 µl of mushroom tyrosinase (0.2 U/µl, 10 U per reaction), and allowed to proceed for 15 minutes. Accumulation of colored product was monitored by light absorption at 450 nm using Victor 2 plate reader (Perkin-Elmer Inc.).

Results

The assays were performed in triplicate and covered a concentration range of test compounds from 4 µM to 5.5 nM. Mean (n=3) absorption of wells containing no enzyme was subtracted as blanks. The data was computed as percentage activity of wells that contained the tyrosinase, but no test compounds. $IC_{50}$ values were computed from non-linear regression fits using GraphPad Prism software. The results for representative compounds of Formulas I-IV are set forth in Tables 1-4 below, and FIGS. 1-9.

Example 7. Murine Melanoma Cell-Based Assays

Selected compounds were then tested for the ability to suppress melanin production by the murine melanoma cells B16-F1 as detailed below.

Materials

Murine melanoma cells B16-F1 were purchased from the ATCC (Cat # CRL-6323). CellTiter96 AqueousOne Solution was purchased from Promega (Cat# G3581). 0.2 µm pore size, low protein binding filters were purchased from PALL Life Sciences. (Cat # PN4454). Alpha-MSH was purchased from the Bachem Inc. (Cat # H-1075.0005). All tissue culture reagents were purchased from the Invitrogen Inc.

The B16-F1 cells were maintained in cell growth media (DMEM/High Glucose supplemented with glutamine, sodium pyruvate, 10% dialyzed fetal calf serum, 1% non-essential amino acids, 50 units/mL penicillin, and 50 µg/mL of streptomycin) at 37° C. in a humidified atmosphere of 95% air and 5% $CO_2$.

All test compounds were initially dissolved in 100% DMSO at a concentration of 400 mM. Then, 6 µl of 400 mM test compounds were added to 1.2 mL of the cell growth media supplemented with 200 nM alpha-MSH, giving a final concentration of 2 mM for the test compound and concentration of 0.5% for DMSO. The compounds were centrifuged for 1 h at 20,000×g. Supernatants (1 mL) were collected and filtered through sterile 0.2 µm filters. The compounds were serially diluted in two-fold increments in the sterile cell growth media supplemented with 0.5% DMSO and 200 nM alpha-MSH, thus keeping the concentration of alpha-MSH and DMSO constant for all samples. These serially diluted compounds were subsequently used as two-fold concentrated stock solutions in the melanin production and cell viability assays.

Methods

B16-F1 cells were seeded into the wells of clear-bottom 96-well plates at 40,000 cells per well, in 100 µl of the cell growth media. On the following day, 100 µl of freshly prepared two fold concentrated test compounds were added to the wells. The cells were maintained at 37° C. in a humidified atmosphere of 95% air and 5% $CO_2$ for 72 hours. At the end of the incubation period melanin-containing conditioned media was removed from the cells and transferred to another plate. To measure melanin content the light absorbance of conditioned media was taken at 450 nm using a Victor 2 plate reader (Perkin-Elmer Inc.).

Viability of cells was measured using standard tetrazolium reduction assay based on redox potential of live cells. After aspiration of melanin-containing conditioned media, the cells were immediately replenished with 100 µl of fresh media supplemented with 16% CellTiter96 AqueousOne solution containing tetrazolium salts. The cells were maintained at 37° C. for additional 20-40 minutes. Conversion of tetrazolium was monitored by measuring absorbance of cell wells at 450 nm using a Victor 2 plate reader (Perkin-Elmer Inc.

Results

The results of the representative experiments are summarized in Table 5 and FIGS. 1-9. More than 90% percent of the melanin produced by cultured melanoma cells is found in extra-cellular media. Therefore, at the end of the experiment melanin-containing media was collected and relative amounts of melanin were determined by adsorption at 450 nm. Viability of cells was determined by a commonly used colorimetric procedure that is based on conversion of the tetrazolium compounds to colored formazan products (using Promega's CellTiter96 AqueousOne assay). Dehydrogenase enzymes in metabolically active cells accomplish this conversion, and the amount of formazan product is directly proportional to the number of living cells in culture.

The assays were performed in quadruplicate and covered a concentration range of test compounds from 2 µM to 1000 µM. Mean (n=4) absorption of wells containing no cells was subtracted as blanks. The results were computed as percent of wells that contained the cells but no test compounds. $IC_{50}$ values were computed from non-linear regression fits using GraphPad Prism software. The results are set forth in Table 5.

TABLE 5

Results of Mushroom Tyrosinase Assay, Melanin Production Assay and Cell Viability Studies for representative compounds of Formulas I-IV

| Compound | Structure | Mushroom Tyrosinase Assay | Melanin production | Cell viability |
|---|---|---|---|---|
| 7 | 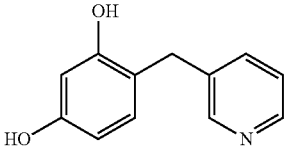 [SMILES: Oc1ccc(Cc2cccnc2)c(O)c1] | IC$_{50}$: = 2.0 μM | IC$_{50}$: = 14 μM | |
| 15 | 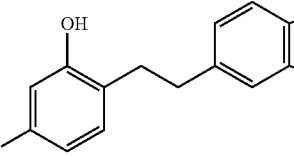 | IC$_{50}$: = 0.25 μM | IC$_{50}$: = 3.3 μM | LD$_{50}$: = 66 μM |
| 16 | 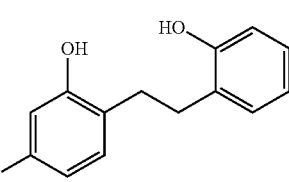 | IC$_{50}$: = 0.35 μM | IC$_{50}$: = 1.7 μM | LD$_{50}$: = 260 μM |
| 17 | 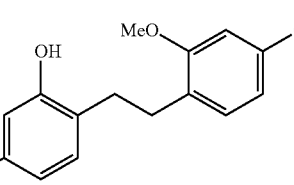 | IC$_{50}$: = 3.0 μM | IC$_{50}$: = 11.9 μM | LD$_{50}$: = 157.8 μM |
| 18 | 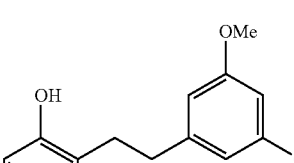 | IC$_{50}$: = 2.8 μM | IC$_{50}$: = 2.97 μM | LD$_{50}$: = 222.2 μM |
| 19 | 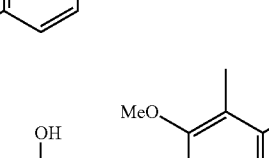 | IC$_{50}$: = 0.80 μM | IC$_{50}$: = 24.7 μM | LD$_{50}$: = 130.3 μM |
| 24 | 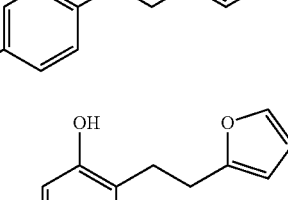 | IC$_{50}$: = 0.2 μM | IC$_{50}$: = 1.60 μM | LD$_{50}$: = 345.9 μM |
| 25 | 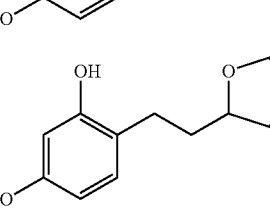 | IC$_{50}$: = 4.5 μM | IC$_{50}$: = 5 μM | LD$_{50}$: >1000 μM |

TABLE 5-continued

Results of Mushroom Tyrosinase Assay, Melanin Production Assay and Cell Viability Studies for representative compounds of Formulas I-IV

| Compound | Structure | Mushroom Tyrosinase Assay | Melanin production | Cell viability |
|---|---|---|---|---|
| 31 | [structure: biphenyl-derived compound with OH, OMe, HO, MeO, OMe substituents] | $IC_{50}: = 0.165\ \mu M$ | $IC_{50}: = 156.1\ \mu M$ | $LD_{50}: = 187.8\ \mu M$ |
| kojic acid | [structure of kojic acid] | $IC_{50}: = 20\ \mu M$ | $IC_{50}: = 303.5\ \mu M$ | $LD_{50}: = >1000\ \mu M$ |

Example 8. Reconstructed Human Skin Studies

Materials and Methods

The skin whitening effects of test compounds were studied using a reconstructed skin model, Melanoderm™ provided by MatTek Corp. (Ashland, Mass.) according to the manufacturer's specifications. Briefly, normal human epidermal keratinocytes and normal human melanocytes derived from dark skin donors were co-cultured on a surface of collagen-coated membrane to form multi-layered, highly differentiated skin tissue (MEL-300-B). The tissues were maintained in the $CO_2$ incubator at 37° C. The apical surfaces of the reconstructed skin (9 mm in diameter) were exposed to air whereas the bottom surfaces remained in contact with 5 mL of maintenance medium, containing skin differentiating factors (EPI-100-NNM-113). Test compounds were formulated in 80% propylene glycol as follows: 10 mg of each test compound was dissolved overnight in 1 mL of propylene glycol (1,2-propanediol, Sigma-Aldrich). The compounds were then sterilized by passing through 0.2 μm filter and diluted in sterile water/propylene glycol to final concentrations 0.2%. 0.4% and 0.8%. The concentration of propylene glycol was kept 80% for all samples. In addition the following controls were used: sterile water, 80% propylene glycol, and 1% kojic acid in water.

Test compounds were applied to the apical surface of the tissues as follows: 10 μl of each test compound, 10 μl of 80% propylene glycol (vehicle control), 25 μl of sterile water (negative control) and 25 μl of 1% kojic acid (positive control). The samples were re-applied every other day for 15 days. All the samples were tested in duplicate. At the end of the experiment microscopic images were taken using photomicroscope equipped with 25× phase contrast objective and color CCD camera.

Results

The potential skin-whitening properties of test compounds were further explored in a reconstructed skin model. The model consists of normal, human-derived epidermal keratinocytes and melanocytes, which have been co-cultured to form a multilayered, highly differentiated human epidermis. In this study the melanocytes were obtained from a highly pigmented donor. The reconstructed skin was grown at the air-liquid interface, making it possible to mimic topical application of skin whitening agents (FIG. 10A).

Different concentrations of test compounds, 80% propylene glycol (the vehicle control), water (negative control) or 1% kojic acid (positive control) were repeatedly applied topically on the surface of the reconstructed skin for 15 days. Two of the test compounds, namely, compound #16, and compound #25 exhibited significant whitening effects on skin melanocytes, without causing any detectable alterations of cell morphology (FIG. 10B). Of them, compound #16 exhibited the greatest effect with significant whitening of melanocytes observed as early as 3 days after the beginning of the experiment (data not shown). Photographs of skin specimen taken after 15 days of the experiment show significant dose-dependent whitening effects on melanocytes, which appear on photographs as dark dendritic cells.

The invention claimed is:

1. A compound selected from 4'-methoxybiphenyl-2,4-diol, and 4-(4'-hydroxybiphenyl)benzene-1,3-diol.

2. A method for preventing and treating diseases and conditions related to the overproduction or uneven distribution of melanin comprising administering to a subject in need thereof an effective amount of a composition comprising one or more compounds selected from the group consisting of 4'-methoxybiphenyl-2,4-diol, and 4-(4'-hydroxybiphenyl)benzene-1,3-diol.

3. The method of claim 2, wherein the diseases and conditions are selected from the group consisting of damage resulting from exposure to the sun or ultraviolet (UV) radiation, suntan, hyper pigmentation spots caused by skin aging, melasma, liver diseases, thermal burns and topical wounds, skin pigmentation due to inflammatory conditions cased by fungal, microbial and viral infections, vitilago, carcinoma, melanoma.

4. A composition comprising the compound of claim 1 and a pharmaceutically or cosmetically acceptable carrier.

5. A method of inhibiting the browning or color changes in fruits, vegetables, juices and other fruit products by administering a composition comprising the compound of claim 1.

6. A method of inhibiting the activity of tyrosinase in a patient by administering a composition comprising the compound of claim 1.

7. A method of inhibiting the activity of melanin in a patient by administering a composition comprising the compound of claim 1.

8. A method of whitening, lightening, or a combination thereof, the skin of a patient by administering a composition comprising the compound of claim 1.

\* \* \* \* \*